(12) United States Patent
Heyward et al.

(10) Patent No.: US 11,738,001 B2
(45) Date of Patent: Aug. 29, 2023

(54) PHARMACEUTICAL COMBINATIONS AND METHODS FOR THE TREATMENT OF DIABETES AND ASSOCIATED DISORDERS

(71) Applicant: OTAGO INNOVATION LIMITED, Dunedin (NZ)

(72) Inventors: Philip Myers Heyward, Dunedin (NZ); Alexander Tups, Dunedin (NZ)

(73) Assignee: OTAGO INNOVATION LIMITED, Dunedin (NZ)

( * ) Notice: Subject to any disclaimer, the term of this patent is extended or adjusted under 35 U.S.C. 154(b) by 232 days.

(21) Appl. No.: 15/733,131

(22) PCT Filed: Nov. 26, 2018

(86) PCT No.: PCT/NZ2018/050169
§ 371 (c)(1),
(2) Date: May 22, 2020

(87) PCT Pub. No.: WO2019/103629
PCT Pub. Date: May 31, 2019

(65) Prior Publication Data
US 2020/0289453 A1     Sep. 17, 2020

(30) Foreign Application Priority Data
Nov. 24, 2017 (NZ) .............................. 2017904756

(51) Int. Cl.
| A61K 31/343 | (2006.01) |
| A61P 3/10 | (2006.01) |
| A61K 31/121 | (2006.01) |
| A61K 36/28 | (2006.01) |

(52) U.S. Cl.
CPC .......... *A61K 31/343* (2013.01); *A61K 31/121* (2013.01); *A61K 36/28* (2013.01); *A61P 3/10* (2018.01); *A61K 2236/331* (2013.01)

(58) Field of Classification Search
None
See application file for complete search history.

(56) References Cited

FOREIGN PATENT DOCUMENTS

| AU | 2015100662 A4 | 6/2015 |
| KR | 1020110119141 A | 11/2011 |
| WO | 2005011671 A1 | 2/2005 |
| WO | 2008055445 A1 | 5/2008 |
| WO | 2008150074 A2 | 12/2008 |
| WO | WO 2008/150074 | * 12/2008 | ............. A61K 36/22 |
| WO | 2008150074 A3 | 1/2009 |
| WO | 2015158836 A1 | 10/2015 |

OTHER PUBLICATIONS

Gupta et al (Int J Pharmacy and Tech 4:5038-5045, 2013) (Year: 2013).*
Lacasse et al (Textile Chemicals, Environmental Data and Facts, 2004—p. 327) (Year: 2004).*
Do et al (J Food and Drug Analysis 22:296-302, 2014) (Year: 2014).*
Kosasih et al (Procedia Chemistry 16:190-194, 2015) (Year: 2015).*
Gaur, R., et al. "In vivo anti-diabetic activity of derivatives of isoliquiritigenin and liquiritigenin", Phytomedicine (2014), vol. 21, No. 4, pp. 415-422.
Song, M.-Y., et al., "Sulfuretin protects against cytokine-induced beta-cell damage and prevents streptozotocin-induced diabetes", Experimental and Molecular Medicine (2010), vol. 42, No. 9, pp. 628-638.
Saito, N., et al., "Paper-chromatographic identification of flavonoids from a scarlet-flowering dahlia and crystallization of pelargonidin and butein", Botanical Magazine Tokyo (1970), vol. 83, No. 985, pp. 229-232.
International Search Report for PCT/NZ2018/050169, dated Jan. 31, 2019.
European Search Report corresponding to EP18880166.6, dated Jul. 2, 2021; 8 pages.
Khangholi, S., Majid, F., Berwary, N., Ahmad, F., & Aziz, R. (2015). The Mechanisms of Inhibition of Advanced Glycation End Products Formation through Polyphenols in Hyperglycemic Condition. Planta Medica, 82(01/02), 32-45. doi:10.1055/s-0035-1558086.
Peng, F., Du, Q., Peng, C., Wang, N., Tang, H., Xie, X., . . . Chen, J. (2015). A Review: The Pharmacology of Isoliquiritigenin. Phytotherapy Research, 29(7), 969-977. doi:10.1002/ptr.5348.

* cited by examiner

*Primary Examiner* — Craig D Ricci
(74) *Attorney, Agent, or Firm* — Barnes & Thornburg LLP; Ryan L. Marshall

(57) ABSTRACT

The invention relates to pharmaceutical compositions comprising combinations of flavonoids that may be used to treat and/or prevent diabetes and associated diseases, conditions and/or disorders. The invention also relates to methods of treating diabetes and associated diseases, conditions and/or disorders using the pharmaceutical compositions.

6 Claims, 16 Drawing Sheets

Data show means ± SEM. *p ≤ 0.05; p ≤ 0.01; *p ≤ 0.001.

Data show means ± SEM. *$p \leq 0.05$; $p \leq 0.01$; *$p \leq 0.001$.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *p ≤ 0.05; p ≤ 0.01; *p ≤ 0.001.

Data show means ± SEM. *$p \leq 0.05$; $p \leq 0.01$; *$p \leq 0.001$.

Data show means ± SEM. *p ≤ 0.05; p ≤ 0.01; *p ≤ 0.001.

Data show means ± SEM. *p ≤ 0.05; p ≤ 0.01; *p ≤ 0.001.

Flower centre intact          Flower centre full bloom

Data show means ± SEM. *p ≤ 0.05; p ≤ 0.01; *p ≤ 0.001.

PHARMACEUTICAL COMBINATIONS AND METHODS FOR THE TREATMENT OF DIABETES AND ASSOCIATED DISORDERS

CROSS REFERENCE TO RELATED APPLICATIONS

This application is a 371 national phase of PCT/NZ2018/050169, filed Nov. 26, 2018, which claims priority to New Zealand Application No. 2017904756, filed Nov. 24, 2017, the disclosures of which are incorporated, in their entirety, by this reference.

FIELD

The invention relates to combinations of flavonoids that may be used to treat diabetes and associated diseases, conditions and/or disorders, and methods of treatment using the flavonoids.

BACKGROUND

Glucose metabolism involves the various biological processes that store, release, produce and process glucose in the body. A key feature of normal glucose metabolism is a highly regulated concentration of glucose in the blood. The main hormones involved in glucose homeostasis are glucagon and insulin. Glucagon is secreted by α-cells, and β-cells secret pro-insulin, which is later converted into insulin. Insulin production is increased in response to higher concentrations of blood glucose, and triggers multiple pathways to lower blood glucose levels. Glucagon has the opposite activity to insulin. Other hormones involved in glucose metabolism include amylin and incretin hormones, such as glucagon-like peptide-1 (GLP-1).

Diabetes is a disease that results when the normal biological processes involved in glucose metabolism are impaired. The classic causes of the disease are either insufficient insulin production or the body failing to adequately respond to the insulin produced. There are many forms of the disease, with the three main types being: type 1, type 2 and gestational diabetes.

Type 1 diabetes is characterised by the patient being unable to produce enough insulin in the pancreas. The onset of type 1 diabetes is usually in childhood.

Type 2 diabetes begins by a period of insulin resistance, where the function of insulin is reduced in response to blood sugar. As the disease progresses, the amount of insulin produced may also diminish. Prediabetes is a term used to describe a state of abnormally elevated glucose levels between normal glucose metabolism and type 2 diabetes. Over 750 million people worldwide have prediabetes and, for example, it is estimated that 25% of the adult population of New Zealand are prediabetic. The rate of progression from prediabetes to type 2 diabetes is approximately 10% per year and 70% over a lifetime. In patients susceptible to the disease, type 2 diabetes is associated with lifestyle factors, such as excessive sugar consumption and lack of exercise.

Gestational diabetes is a form of the disease that presents in women during pregnancy.

Since 1980, the number of people suffering from type 2 diabetes worldwide has increased fourfold and is predicted to rise further to an estimated number of 552 million people in 2030. The IDF Diabetes Model projects that the total number of people with diabetes will increase from 415 million (2015) to 642 million (2040) resulting in a total annual cost of $802 billion worldwide. Twelve percent of global health expenditure is spent on diabetes treatment and it is predicted that by 2040 one in 10 adults will suffer from this disease. In addition to this enormous economic burden, poorly managed diabetes leads to serious complications and shorter life expectancy. Currently, there are several drugs available for the treatment of type 2 diabetes and most of them are effective in lowering blood glucose levels; however, they partially possess side effects such as hypoglycaemia, weight gain and increased risk of heart failure.

There is therefore a continuing need to develop new therapies for diabetes and associated diseases, conditions and/or disorders, including prediabetes and/or diet-induced impairments in glucose regulation.

SUMMARY

The inventors have found that treatment with a combination of butein or a pharmaceutically acceptable salt, tautomer, solvate and/or derivative thereof (BTN), and either or both of sulfuretin or a pharmaceutically acceptable salt, tautomer, solvate and/or derivative thereof (SLF) and/or isoliquiritigenin or a pharmaceutically acceptable salt, tautomer, solvate and/or derivative thereof (ILQ) may reverse the effects of impairments in glucose regulation, including impairment that is diet-induced. Treatment with these combinations may therefore be useful in the treatment of diabetes and associated diseases, conditions and/or disorders.

In one aspect, the invention provides a pharmaceutical composition comprising BTN and SLF and/or ILQ.

In some embodiments, the combination of BTN and SLF and/or ILQ is provided as an extract of a *Dahlia* plant.

In a further aspect, the invention provides a method of treating diabetes or an associated disease, condition and/or disorder, comprising administering to a subject in need thereof an effective amount of a pharmaceutical composition comprising BTN and SLF and/or ILQ.

In another aspect, the invention provides use of BTN and SLF and/or ILQ in the preparation of a medicament for treating diabetes or an associated disease, condition and/or disorder.

In a further aspect, the invention provides a pharmaceutical composition for use in treating diabetes or an associated disease, condition and/or disorder, the pharmaceutical composition comprising BTN and SLF and/or ILQ.

In another aspect, the invention provides an antidiabetic agent comprising BTN and SLF and/or ILQ.

In a further aspect, the invention provides a method of treating diabetes or an associated disease, condition and/or disorder, comprising administering to a subject in need thereof an effective amount of ILQ.

In another aspect, the invention provides use of ILQ in the preparation of a medicament for treating diabetes or an associated disease, condition and/or disorder.

In a further aspect, the invention provides a pharmaceutical composition for use in treating diabetes or an associated disease, condition and/or disorder, comprising ILQ.

In another aspect, the invention provides an antidiabetic agent comprising ILQ.

In a further aspect, the invention provides a method of treating type 2 diabetes, prediabetes and/or diet-induced impairment of glucose regulation, comprising administering to a subject in need thereof an effective amount of SLF.

In another aspect, the invention provides use of SLF in the preparation of a medicament for treating type 2 diabetes, prediabetes and/or diet-induced impairment of glucose regulation.

In a further aspect, the invention provides a pharmaceutical composition for use in treating type 2 diabetes, prediabetes and/or diet-induced impairment of glucose regulation, comprising SLF.

In yet another aspect, the invention provides an anti-type 2 diabetes and/or prediabetes agent comprising SLF.

BRIEF DESCRIPTION OF DRAWINGS

The present invention will be further described, by way of example only, with reference to the accompanying drawings, in which:

FIG. 10A shows an image of a brain section of a LFD fed mouse treated with vehicle only; FIG. 10B shows an image of a brain section of a LFD fed mouse treated with insulin and vehicle; FIG. 10C shows an image of a brain section of a HFD fed mouse treated with vehicle only; FIG. 10D shows an image of a brain section of a HFD fed mouse treated with insulin and vehicle; FIG. 10E shows an image of a brain section of a HFD fed mouse treated with insulin and a 1:1:1 by weight combination of butein, sulfuretin and isoliquiritigenin; FIG. 10F shows an image of a brain section of a HFD fed mouse treated with insulin and an extract of a *Dahlia* plant. The total number of phosphorylated-protein kinase B (pAKT) immunoreactive cells within the arcuate nucleus (ARC) (framed area) was counted in three region-matched sections for each animal.

FIG. 19A shows a *Dahlia* flowerhead with the centre intact (closed centre), and FIG. 19B shows a *Dahlia* flowerhead in full bloom (open centre).

DESCRIPTION OF EMBODIMENT(S)

Figure 1:
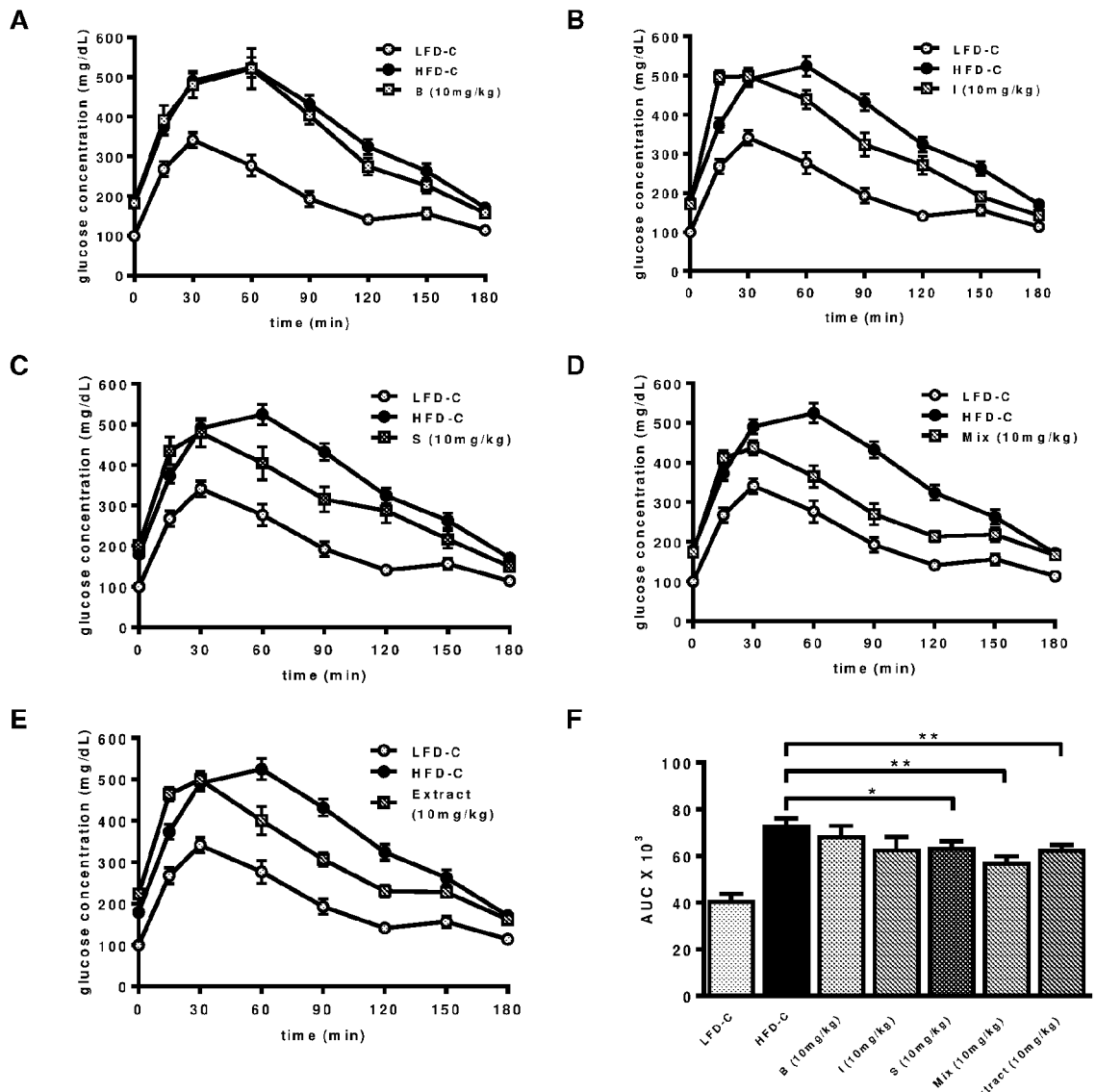
FIGS. 1A-E show graphs of intraperitoneal glucose tolerance test (ipGTT) results on C57BL/6 mice fed (1) a high fat diet (HFD) for 4 weeks; (2) a low fat diet (LFD) for 4 weeks or (3) a high fat diet for 4 weeks and followed by treatment with butein (A), isoliquiritigenin (B), sulfuretin (C), a 1:1:1 mixture of butein, sulfuretin and isoliquiritigenin (D) and an extract of *Dahlia* flower petals (E).
FIG. 1F shows a bar graph comparing the area under the curve for the ipGTT results shown in FIGS. 1A-E.

Before describing the present invention in detail, it is to be understood that this invention is not limited to particularly exemplified embodiments, such as the pharmaceutical compositions, uses thereof or methods of production or treatment, which may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

The term "pharmaceutical composition" relates to a composition comprising at least one active ingredient that is in a pharmaceutically acceptable form. The term "pharmaceutical composition" may encompass compositions intended to be sold as nutraceutical products (e.g. supplements that provide a health benefit). In some embodiments, the pharmaceutical composition is a nutraceutical composition.

By "pharmaceutically acceptable" it is meant that the ingredient is compatible with other ingredients included in the pharmaceutical composition and is suitable for administration to a subject based on avoidance of deleterious effects upon or following administration and any regulatory considerations.

The term "administering" refers to providing the pharmaceutical composition to a subject suffering from or at risk of the disease(s) and/or condition(s) to be treated.

By "effective amount" it is meant an amount sufficient that, when administered to the subject, an amount of the drug is provided to achieve an effect. In the case of a therapeutic method, this effect may be the treatment of diabetes or an associated disease, condition and/or disorder. Therefore, the "effective amount" may be a "therapeutically effective amount". By "therapeutically effective amount" it is meant an amount sufficient that when administered to the subject an amount of active ingredient is provided to treat the disease or a symptom of the disease.

As used herein, the term "diabetes" relates to a disease characterised by insulin resistance and disordered glucose metabolism, and is often accompanied by complications including dyslipidemia, inflammation, retinopathy, neuropathy, nephropathy, macrovascular disease and cognitive impairment. Diabetes includes type 1, type 2 and gestational diabetes and symptoms and/or complications thereof. Type 1 and 2 diabetes are typically characterised by a loss of beta cell function.

As used herein, the terms "treating", "treatment", "treat" and the like mean affecting a subject (e.g. a patient), tissue or cell to obtain a desired pharmacological and/or physiological effect. The effect may be prophylactic in terms of completely or partially preventing, or reducing the severity of, a disease or associated symptom, and/or may be therapeutic in terms of a partial or complete cure of a disease. For example, a reference to "treating" diabetes therefore encompasses: (a) arresting the progress of the disease, e.g. preventing worsening of a symptom or complication over time; (b) relieving or ameliorating the effects of diabetes, i.e. causing an improvement of at least one symptom or complication of diabetes; (c) preventing additional symptoms or complications of diabetes from developing; (d) preventing diabetes or a symptom or complication associated with diabetes from occurring in a subject with prediabetes or insulin resistance; and/or (e) preventing an increased risk of developing a disease, e.g. preventing the increase of a risk factor for diabetes, such as by reducing blood glucose levels following glucose administration.

It must be noted that as used herein and in the appended claims, the singular forms "a," "an," and "the" include plural reference unless the context clearly dictates otherwise.

Thus, for example, a reference to "an excipient" may include one or more excipients, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

The term "(s)" following a noun contemplates the singular or plural form, or both.

The term "and/or" can mean "and" or "or".

Unless the context requires otherwise, all percentages referred to herein are percentages by weight of the pharmaceutical composition.

Unless the context requires otherwise, all amounts referred to herein are intended to be amounts by weight of the pharmaceutical composition.

Various features of the invention are described with reference to a certain value, or range of values. These values are intended to relate to the results of the various appropriate measurement techniques, and therefore should be interpreted as including a margin of error inherent in any particular measurement technique. Some of the values referred to herein are denoted by the term "about" to at least in part account for this variability. The term "about", when used to describe a value, may mean an amount within ±25%, ±10%, ±5%, ±1% or ±0.1% of that value.

The term "comprising" as used in this specification means "consisting at least in part of". When interpreting statements in this specification that include that term, the features, prefaced by that term in each statement, all need to be present but other features can also be present. Related terms such as "comprise" and "comprised" are to be interpreted in the same manner.

Pharmaceutical Compositions

The pharmaceutical compositions comprise a combination of butein or a pharmaceutically acceptable salt, tautomer, solvate and/or derivative thereof (BTN) and either or both of sulfuretin or a pharmaceutically acceptable salt, tautomer, solvate and/or derivative thereof (SLF) and/or isoliquiritigenin or a pharmaceutically acceptable salt, tautomer, solvate and/or derivative thereof (ILQ). Thus the pharmaceutical compositions may comprise BTN and SLF, BTN and ILQ, or BTN, SLF and ILQ.

The inventors surprisingly found that pharmaceutical compositions comprising the combination of BTN and SLF, BTN and ILQ, or BTN, SLF and ILQ were able to treat impairment of glucose regulation. It was also surprising that the combination of SLF and ILQ in the absence of BTN did not possess the same efficacy.

Butein and isoliquiritigenin are chalcones. Sulfuretin is an aurone and, under some conditions is a cyclisation product of butein (see Example 2). Butein, isoliquiritigenin and sulfuretin have been described as being present in extracts of plants. The structures of butein, isoliquiritigenin and sulfuretin are shown in Table 1.

TABLE 1

Chalcones and aurone

| # | Compound Name | Structure |
|---|---|---|
| 1 | Butein | (1) |

TABLE 1-continued

Chalcones and aurone

| # | Compound Name | Structure |
|---|---|---|
| 2 | Iso-liquiritigenin | (2) |
| 3 | Sulfuretin | (3) |

The inventors investigated combinations of BTN, SLF and ILQ as treatments for diet-induced impairment of glucose regulation. Surprisingly, they found that only some of the combinations of these compounds showed efficacy against diet-induced impairment of glucose regulation. It was found that the combination of ILQ and SLF without BTN lacked efficacy in this treatment. Surprisingly, these active combinations also show efficacy against impairment of glucose regulation, even when not solely induced by diet. It is therefore surprising that combinations of BTN and ILQ, BTN and SLF, and BTN, SLF and ILQ possess efficacy in the treatment of diabetes and associated diseases, conditions and/or disorders.

In some embodiments, the relative amount of SLF and/or ILQ may be greater than or equal to the amount of BTN present in the pharmaceutical compositions. The amount of SLF may be 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3 or more times the amount of BTN present in the pharmaceutical compositions. The amount of ILQ may be 1, 1.1, 1.2, 1.3, 1.4, 1.5, 1.6, 1.7, 1.8, 1.9 or 2 times the amount of BTN present in the pharmaceutical compositions. The combined amount of SLF and ILQ may be 1, 1.05 or 1.1 times the amount of BTN present in the pharmaceutical composition.

In some embodiments, the relative amount of SLF or ILQ may be less than the amount of BTN present in the pharmaceutical compositions. The amount of SLF may be 0.3, 0.4, 0.5, 0.6, 0.7, 0.8 or 0.9 times the amount of BTN present in the pharmaceutical compositions. The amount of BTN may be 1.1, 1.2, 1.3, 1.4, 1.5, 1.6, 1.7, 1.8 or more times the amount of SLF present in the pharmaceutical compositions. The amount of ILQ may be 0.3, 0.4, 0.5, 0.6, 0.7, 0.8 or 0.9 times the amount of BTN present in the pharmaceutical compositions. The amount of BTN may be 1.1, 1.2, 1.3, 1.4, 1.5, 1.6, 1.7 or more times the amount of ILQ present in the pharmaceutical compositions.

The weight ratio of SLF to BTN may be 0.4:1, 0.5:1, 0.6:1, 0.7:1 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1, 3:1, 3.1:1, 3.2:1, 3.3:1, 3.4:1, 3.5:1, 3.6:1, 3.7:1, 3.8:1, 3.9:1, 4:1, 4.1:1, 4.2:1, 4.3:1, 4.4:1, 4.5:1, 4.6:1, 4.7:1, 4.8:1, 4.9:1 or 5:1. The weight ratio of SLF to BTN may be between any of these weight ratios, for example, the weight ratio of SLF to BTN may be from 1:1 to 5:1, 1:1 to 2.5:1 or 1.5:1 to 2.5:1. The weight ratio may alternatively be expressed as a single numeral which may be calculated by dividing the amount of SLF by the amount of BTN. Expressed in this way, the amount of SLF to BTN may be 0.4, 0.5, 0.6, 0.7, 0.8. 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 or greater. In this context, a greater weight ratio means greater amounts of SLF compared to BTN present in the pharmaceutical compositions.

The weight ratio of ILQ to BTN may be 0.4:1, 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, or 2:1, 2.1:1, 2.2:1, 2.3:1, 2.4:1, 2.5:1, 2.6:1, 2.7:1, 2.8:1, 2.9:1 or 3:1. The weight ratio of ILQ to BTN may be between any of these weight ratios, for example, the weight ratio of ILQ to BTN may be from 1:1 to 3:1, 1:1 to 1.8:1, 0.5:1 to 0.8:1 or 1.2:1 to 1.8:1. The weight ratio may alternatively be expressed as a single numeral which may be calculated by dividing the amount of ILQ by the amount of BTN. Expressed in this way, the amount of ILQ to BTN may be 0.4, 0.5, 0.6, 0.8. 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3 or higher. In this context, a higher weight ratio means greater amounts of ILQ compared to BTN.

In embodiments comprising the combination of BTN, SLF and ILQ the ratio of SLF:ILQ:BTN may be determined based on any combination of the above ratios of SLF:BTN and ILQ:BTN, for example, the ratio of SLF:BTN:ILQ may be 1:1:1, 1:1.8:1.1, 1:1.8:1, 1:2:1, 1:2:1.1, 1.1:1.8:1, 5:3:1, 2.5:2:1, 2.5:1.4:1, 2:2:1, 1.4:1:1.1, 2:1:1.6 or 2:1.4:1. The ratio of SLF:ILQ:BTN may be between any of these weight ratios, for example, the weight ratio of BTN:SLF:ILQ may be from 1:1:1 to 5:3:1, 1:1:1 to 2.5:2:1, 1:1:1 to 2:1:1, 1:1:1 to 1:2:1, 1:1:1 to 1:1.5:1, 1:1:1 to 2:1.4:1, 1:1:1 to 2:1:1.6 or 1.1:1.1:1 to 5:3:1.

In some embodiments of the pharmaceutical compositions comprising the combination of BTN, SLF and ILQ, the amount of BTN is greater than or equal to the amount of SLF or ILQ present in the pharmaceutical compositions. In these embodiments, the ratio of BTN:SLF may be about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 3:1, 3.5:1, 4:1, 4.5:1, 5:1 or greater. The ratio of BTN:SLF may be from any of these ratios to any other of these ratios, for example, from about 1.1:1 to about 5:1 or about 1.5:1 to about 2:1. In these embodiments, the ratio of BTN:ILQ may be about 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 3:1, 3.5:1, 4:1, 4.5:1, 5:1 or greater. The ratio of BTN:ILQ may be from any of these ratios to any other of these ratios, for example, from about 1.1:1 to about 5:1 or about 1.8:1 to about 2.5:1.

In some embodiments, in pharmaceutical compositions comprising the combination of BTN, SLF and ILQ, the amount of SLF is greater than or equal to the amount of ILQ present in the pharmaceutical compositions. In other embodiments of pharmaceutical compositions comprising the combination of BTN, SLF and ILQ, the amount of ILQ is greater than or equal to the amount of SLF present in the pharmaceutical compositions. In some embodiments of pharmaceutical compositions comprising BTN, SLF and ILQ, the amount of SLF and ILQ is balanced, such as within about 5% or 10% of each other based on the total weight of the composition. In embodiments, comprising a combination of BTN, SLF and ILQ, the weight ratio of SLF:ILQ may be about 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.5:1, 3:1, 3.5:1, 4:1, 4.5:1 or 5:1. The ratio of SLF:ILQ may be between any of these weight ratios, for example, the weight ratio of SLF:ILQ may be from 0.5:1 to 5:1, 0.6:1 to about 3:1 or 0.8:1 to 1:1. The weight ratio may alternatively be expressed as a single numeral which may be calculated by dividing the amount of SLF by the amount of ILQ. Expressed in this way, the amount of SLF to ILQ may be 0.5, 0.6, 0.8. 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3 or higher. In this context, a higher weight ratio means greater amounts of SLF compared to ILQ.

The pharmaceutical compositions may comprise BTN in an amount of at least about 0.001 wt %, about 0.005 wt %, about 0.01 wt % about 0.05 wt %, about 0.1 wt %, about 0.15 wt %, about 0.5 wt %, about 1 wt %, about 2 wt %, about 3 wt %, about 3.3 wt %, about 4 wt %, about 5 wt %, about 6 wt %, about 6.7 wt %, about 7 wt %, about 8 wt %, about 9 wt % or about 10 wt %. The maximum amount of BTN present in the pharmaceutical compositions may be up to about 99.999 wt %, about 99 wt %, about 98 wt %, about 70 wt %, about 50 wt %, about 30 wt %, about 25 wt %, about 20 wt %, about 15 wt %, about 10 wt %, about 5 wt %, about 4 wt %, about 3 wt % or about 2 wt %. The pharmaceutical compositions may comprise BTN in an amount from any of these minimum amounts to any of these maximum amounts, for example, the pharmaceutical compositions may comprise BTN in an amount from about 0.001 wt % to about 99 wt %, about 1 wt % to about 99 wt %, about 1 wt % to about 98 wt %, about 1 wt % to about 70 wt %, about 1 wt % to about 50 wt %, about 1 wt % to about 30 wt %, about 1 wt % to about 25 wt %, about 1 wt % to about 20 wt %, about 2 wt % to about 20 wt %, about 5 wt % to about 20 wt %, about 5 wt % to about 15 wt %, about 0.001 wt % to about 5 wt %, about 0.01 wt % to about 5 wt %, about 0.1 wt % to about 5 wt %, or about 0.1 wt % to about 2 wt %.

The pharmaceutical compositions may comprise SLF in an amount of at least about 0.001 wt %, about 0.005 wt %, about 0.01 wt % about 0.05 wt %, about 0.1 wt %, about 0.5 wt %, about 1 wt %, about 2 wt %, about 3 wt %, about 3.3 wt %, about 4 wt %, about 5 wt %, about 6 wt %, about 6.7 wt %, about 7 wt %, about 8 wt %, about 9 wt % or about 10 wt %. The maximum amount of SLF present in the composition may be up to about 99.999 wt %, about 99 wt %, about 98 wt %, about 70 wt %, about 50 wt %, about 30 wt %, about 25 wt %, about 20 wt %, about 15 wt %, about 10 wt %, about 5 wt %, about 4 wt %, about 3 wt %, about 2 wt %, about 1.5 wt % or about 1 wt %. The pharmaceutical compositions may comprise SLF in an amount from any of these minimum amounts to any of the maximum amounts, for example, the pharmaceutical compositions may comprise SLF in an amount from about 0.001 wt % to about 99 wt %, about 1 wt % to about 99 wt %, about 1 wt % to about 98 wt %, about 1 wt % to about 70 wt %, about 1 wt % to about 50 wt %, about 1 wt % to about 30 wt %, about 1 wt % to about 25 wt %, about 1 wt % to about 20 wt %, about 2 wt % to about 20 wt %, about 5 wt % to about 20 wt %, about 5 wt % to about 15 wt %, about 0.001 wt % to about 5 wt %, about 0.01 wt % to about 5 wt %, about 0.1 wt % to about 5 wt %, about 0.1 wt % to about 2 wt % or about 0.1 wt % to about 1 wt %.

The pharmaceutical compositions may comprise ILQ in an amount of at least about 0.001 wt %, about 0.005 wt %, about 0.01 wt % about 0.05 wt %, about 0.1 wt %, about 0.5 wt %, about 1 wt %, about 2 wt %, about 3 wt %, about 3.3 wt %, about 4 wt %, about 5 wt %, about 6 wt %, about 6.7 wt %, about 7 wt %, about 8 wt %, about 9 wt % or about 10 wt %. The maximum amount of ILQ present in the pharmaceutical compositions may be up to about 99.999 wt %, about 99 wt %, about 98 wt %, about 70 wt %, about 50 wt %, about 30 wt %, about 25 wt %, about 20 wt %, about 15 wt %, about 10 wt %, about 5 wt %, about 4 wt %, about 3 wt %, about 2 wt %, about 1.5 wt % or about 1 wt %. The pharmaceutical compositions may comprise ILQ in an amount from any of these minimum amounts to any of the maximum amounts, for example, the pharmaceutical compositions may comprise ILQ in an amount from about 0.001 wt % to about 99 wt %, about 1 wt % to about 99 wt %, about 1 wt % to about 98 wt %, about 1 wt % to about 70 wt %, about 1 wt % to about 50 wt %, about 1 wt % to about 30 wt %, about 1 wt % to about 25 wt %, about 1 wt % to about 20 wt %, about 2 wt % to about 20 wt %, about 5 wt % to about 20 wt %, about 5 wt % to about 15 wt %, about 0.001 wt % to about 5 wt %, about 0.01 wt % to about 5 wt %, about 0.1 wt % to about 5 wt %, about 0.1 wt % to about 2 wt % or about 0.1 wt % to about 1.5 wt %.

In some embodiments, the pharmaceutical compositions optionally comprise one or more pharmaceutically acceptable excipient(s). The excipient may be a carrier, diluent, adjuvant, stabiliser or other excipient, or any combination thereof.

In some embodiments, the pharmaceutically acceptable excipient is a stabiliser, for example, a stabiliser capable of preventing the conversion of BTN to SLF when in the form of a liquid, e.g. liquid administration forms or liquid forms prepared as intermediates to the final form of the pharmaceutical compositions. The stabiliser may be natural or non-natural (e.g. synthetic or semi-synthetic). Suitable stabilisers include polar organic solvents, including dimethylsulphoxide and alcohols such as methanol, ethanol, propanol (including iso- and tert-propanol), butanol (including iso-, sec- and tert-butanol); pH<4 buffers (e.g. an aqueous buffer, such as a phosphate buffered saline (PBS) of pH4 or less); or a combination thereof.

The pharmaceutical compositions may be formulated, for example, by employing conventional solid or liquid vehicles or diluents, as well as pharmaceutical additives of a type appropriate to the mode of desired administration (for example, excipients, binders, preservatives, stabilisers, flavours, etc.) according to techniques such as those well known in the art of pharmaceutical formulation (see, for example, Remington: The Science and Practice of Pharmacy, 21st Ed., 2005, Lippincott Williams & Wilkins). The pharmaceutically acceptable carrier may be any carrier included in the United States Pharmacopeia/National Formulary (USP/NF), the British Pharmacopoeia (BP), the European Pharmacopoeia (EP), the Japanese Pharmacopoeia (JP) or the Chinese Pharmacopoeia (ChP). In some embodiments, the excipient may be non-natural (e.g. synthetically produced).

The pharmaceutical compositions may be administered by any suitable route of administration, and may therefore be formulated in a form suitable for any such route of administration. For example, the route of administration may be oral, rectal, nasal, topical (including buccal and sub-lingual), vaginal or parenteral (including intramuscular, subcutaneous, intraperitoneal and intravenous) administration or administration by inhalation or insufflation.

The pharmaceutical compositions may be prepared in unit dosage form. In such form, the pharmaceutical compositions are subdivided into unit doses containing appropriate quantities of the active ingredient(s). The unit dosage form can be a packaged preparation, the package containing discrete quantities of preparation. The preparation may be a solid, such as packeted tablets, capsules (e.g. filled capsules), lozenges, powders in vials or ampoules, or a liquid, such as solutions, suspensions, emulsions, elixirs, or capsules filled with the same. Also, the unit dosage form can be a capsule, tablet, cachet, or lozenge itself, or it can be the appropriate number of any of these in packaged form.

The pharmaceutical compositions, including when prepared as unit dosage forms, may comprise conventional ingredients in conventional proportions, with or without additional active ingredient(s), and such unit dosage forms may contain any suitable effective amount of the active ingredients commensurate with the intended daily dosage range to be employed.

For preparing pharmaceutical compositions described herein, pharmaceutically acceptable carriers can be either solid or liquid. Solid form preparations include powders, tablets, pills, capsules, cachets, suppositories, lozenges and dispensable granules. A solid carrier can be one or more substances which may also act as diluents, flavouring agents, solubilisers, lubricants, suspending agents, binders, preservatives, tablet disintegrating agents, or an encapsulating material.

Suitable carriers include magnesium carbonate, magnesium stearate, talc, sugar, lactose, pectin, dextrin, starch (e.g. maize starch, potato starch, etc.), gelatin, tragacanth, methylcellulose, sodium carboxymethylcellulose, a low melting wax, cocoa butter, microcrystalline cellulose (MCC), silicified microcrystalline cellulose, powdered cellulose, alginate, polydextrose, calcium sulfate dihydrate, calcium hydrogen phosphate dihydrate, colloidal silicon dioxide, talc, hydroxypropyl methylcellulose (HPMC), hydroxypropyl methylcellulose acetate succinate (HPMCAS), polyvinylpyrrolidone (PVP), acrylates and methacrylates, polyethylene glycol (PEG), polyethylene oxide (PEO), acacia gum and the like. Tablets, powders, capsules, pills, cachets, and lozenges can be used as solid forms suitable for oral administration. In some embodiments, the pharmaceutical composition comprises the active ingredient(s) and a carrier, such as MCC.

Liquid form preparations include solutions, dispersions, suspensions, and emulsions, for example, water or water-propylene glycol solutions. For example, parenteral injection liquid preparations can be formulated as solutions in aqueous polyethylene glycol solution. Liquid preparations are preferred for embodiments involving sub-lingual administration.

Sterile liquid form pharmaceutical compositions include sterile solutions, suspensions, emulsions, syrups and elixirs. The active ingredient(s) may be suspended in a pharmaceutically acceptable carrier, such as sterile water, sterile organic solvent or a mixture of both.

Aqueous solutions can be prepared by dissolving the active ingredient(s) in water and adding suitable colorants, flavours, stabilising and thickening agents, as desired. Aqueous suspensions can be made by dispersing the finely divided active ingredient(s) in water with viscous material, such as natural or synthetic gums, resins, methylcellulose, sodium carboxymethylcellulose, or other well-known suspending agents.

In some embodiments, the administration of the pharmaceutical compositions is oral administration. The pharmaceutical compositions may be formulated for oral administration in any suitable form. For example, pharmaceutical compositions for oral administration may be formulated in one or more of the following forms: a tablet, a troche, a powder, a granulate, a lozenge, a solution, a suspension, an emulsion, an elixir, a syrup, a wafer or a capsule filled with a solution, a suspension, an emulsion, an elixir, a syrup, a powder, a granulate or a combination thereof. Typically suitable oral forms of the pharmaceutical compositions will comprise one or more pharmaceutically acceptable excipient(s).

The tablets, troches, pills, lozenges, capsules and the like may also contain any of the components as listed hereafter: a binder such as acacia gum, corn starch or gelatin; excipients such as dicalcium phosphate, microcrystalline cellulose (MCC), silicified microcrystalline cellulose or powdered cellulose; a disintegrating agent such as corn starch, potato starch, alginic acid, alginate, polyvinyl pyrrolidone (PVP) and the like; a lubricant such as magnesium stearate; and a sweetening agent such a sucrose, lactose or saccharin may be added or a flavouring agent such as peppermint, oil of wintergreen, or cherry flavouring. When the dosage unit form is a capsule, it may contain, in addition to materials of the above type, a liquid carrier.

In some embodiments, the dosage unit form is a capsule. To form a capsule, typically the active ingredient(s) are combined with one or more of the excipients (e.g. carriers) described herein to provide a solid or liquid formulation, which is then encased within a capsule shell. Any suitable capsule shell known in the art may be used, including hard and soft capsule shells. Suitable hard capsule shells may comprise gelatine, HPMC, starch, pullulan and/or polyvinyl acetate (PVA). Suitable soft capsules may comprise gelatin thickened with a thickening agent, such as a polyol (e.g. glycerine or sorbitol). As noted above, the capsule shell may be filled with any of the following dosage forms described herein: a solution, a suspension, an emulsion, an elixir, a syrup, a powder, a granulate or a combination thereof. When the capsule is filled with a solid dosage form, it may be dried prior to filling. In some embodiments, the solid dosage form is freeze-dried prior to filling the capsule shell. Alternatively, a liquid excipient may be added to an otherwise dry solid dosage form to provide a wet dosage form, such as a granulate, a solution, a suspension, an emulsion, an elixir or a syrup.

Various other materials may be present as coatings or to otherwise modify the physical form of the dosage unit. For instance, tablets, pills, or capsules may be coated with shellac, sugar or both. A syrup or elixir may contain the active ingredient(s), sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active ingredient(s) may be incorporated into sustained-release preparations and formulations, including those that allow specific delivery of the active ingredient(s) to specific regions of the gut.

Also included are solid form preparations that are intended to be converted, shortly before use, to liquid form preparations, such as for oral and/or sub-lingual administration. Such liquid forms include solutions, suspensions, and emulsions. These preparations may contain, in addition to the active ingredient(s), colorants, flavours, stabilisers, buffers, artificial and natural sweeteners, dispersants, thickeners, solubilising agents, and the like.

In formulations intended for administration to the respiratory tract, including intranasal formulations, the pharmaceutical compositions may have a small particle size for example of the order of 5 to 10 microns or less. Such a particle size may be obtained by means known in the art, for example by micronisation.

Administration to the respiratory tract may be achieved by means of an aerosol formulation in which the active ingredient(s) are provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas.

The aerosol may conveniently also contain a surfactant. The dose of drug may be controlled by provision of a metered valve.

Alternatively the active ingredient(s) may be provided in the form of a dry powder, for example a powder mix of the active ingredient(s) in a suitable powder base such as lactose, starch, starch derivatives such as hydroxypropylmethyl cellulose and polyvinylpyrrolidone (PVP). The pharmaceutical compositions in powder form may be presented in unit dose form for example in capsules or cartridges of, e.g. gelatin, or blister packs.

In the case of a spray, this may be achieved for example by means of a metering atomising spray pump. For such sprays, active ingredient(s) may be encapsulated with cyclodextrins, or formulated with other agents expected to enhance delivery and retention in the nasal mucosa.

Formulations suitable for topical administration in the mouth (e.g. sub-lingual administration) include any liquid formulation described herein, preferably liquid formulations with a viscosity suitable for administration by dropper or syringe; lozenges comprising active ingredient(s) in a flavoured base, usually sucrose and acacia or tragacanth; pastilles comprising the active ingredient(s) in an inert base such as gelatin and glycerin or sucrose and acacia; and mouthwashes comprising the active ingredient(s) in a suitable liquid carrier.

For administration to the nasal cavity, solutions or suspensions may be applied directly to the nasal cavity by conventional means, for example with a dropper, pipette or spray. The formulations may be provided in single or multidose form. In the latter case of a dropper or pipette, this may be achieved by the subject administering an appropriate, predetermined volume of the solution or suspension.

For topical administration to the epidermis the active ingredient(s) may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

The pharmaceutical compositions may be formulated for parenteral administration (e.g. by injection, for example bolus injection or continuous infusion) and may be presented in unit dose form in ampoules, pre-filled syringes, small volume infusion or in multi-dose containers optionally with an added preservative. The pharmaceutical compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

Pharmaceutical compositions for parenteral administration may also be provided in unit dosage form for ease of administration and uniformity of dosage. Unit dosage form as used herein refers to physically discrete units suited as unitary dosages for the subjects to be treated; each unit containing a predetermined quantity of active material calculated to produce the desired therapeutic effect in association with the required pharmaceutical excipient. The specification for the unit dosage forms are dictated by and directly dependent on (a) the unique characteristics of the active ingredient(s) and the particular therapeutic effect to be achieved, and (b) the limitations inherent in the art of compounding such an active ingredient(s) for the treatment of living subjects having a diseased condition in which bodily health is impaired.

Administration forms suitable for injectable use include sterile injectable solutions or dispersions, and sterile powders for the extemporaneous preparation of sterile injectable solutions. They should be stable under the conditions of manufacture and storage and may be preserved against oxidation and the contaminating action of microorganisms such as bacteria or fungi.

The solvent or dispersion medium for the injectable solution or dispersion may contain any of the conventional solvent or carrier systems, and may contain, for example, water, ethanol, polyol (for example, glycerol, propylene glycol and liquid polyethylene glycol, and the like), suitable mixtures thereof, and vegetable oils.

Administration forms suitable for injectable use may be delivered by any appropriate route including intravenous, intramuscular, intracerebral, intrathecal, intraperitoneal, epidural injection or infusion.

Sterile injectable solutions are prepared by incorporating the active ingredients in the required amount in the appropriate carrier with various other ingredients such as those enumerated above, as required, followed by sterilisation. Generally, dispersions are prepared by incorporating the various sterilised active ingredients into a sterile vehicle which contains the basic dispersion medium and the required other ingredients from those enumerated above. In the case of sterile powders for the preparation of sterile injectable solutions, preferred methods of preparation are vacuum drying or freeze-drying of a previously sterile suspension of the active ingredient plus any additional desired ingredients.

In some embodiments, the pharmaceutical compositions are provided in the form of a food product. Suitable food products include solid food products including baked goods and liquid food products such as a beverage. The active ingredient(s) may be incorporated into the food product during manufacture or may be added to an existing product. Therefore, the food products disclosed herein may comprise BTN and SLF and/or ILQ and at least one Generally Recognised As Safe (GRAS) ingredient. The GRAS ingredient may be any ingredient included in the GRAS database maintained by the US Food and Drug Administration (FDA).

For any route of administration, the amount of active ingredient(s) in therapeutically useful pharmaceutical compositions should be sufficient that a suitable dosage will be obtained. Accordingly, the active ingredient(s) are preferably provided in an effective amount.

Pharmaceutically acceptable carriers and/or diluents include any and all solvents, dispersion media, coatings, antibacterial and antifungal agents, isotonic and absorption delaying agents and the like.

When desired, formulations adapted to give sustained release of the active ingredient(s) may be employed.

The practice of the present invention employs, unless otherwise indicated, conventional pharmaceutical and/or medical techniques within the skill of the art. Such techniques are well known to the skilled worker, and are explained fully in the literature.

*Dahlia* Extracts

BTN, SLF and ILQ may be combined from purified forms of the compounds, which may be purified after extraction from a natural source, or produced synthetically or semi-synthetically. Butein (Sigma), isoliquiritigenin (AK Scientific) and sulfuretin (BBP) are commercially available. Any means known in the art for producing BTN, SLF and ILQ is contemplated, for example, SLF may be obtained by oxidative cyclisation of BTN (see, e.g. Example 2).

The inventors found that extracts of a *Dahlia* plant are able to provide combinations of BTN and SLF and/or ILQ. The activity of these extracts is shown to be comparable to that of pharmaceutical compositions comprising 1:1:1 SLF:ILQ:BTN (see Example 1; Experiments 4 and 5).

The relative amount of BTN, SLF and ILQ in an extract may be determined using standard techniques in the art, such as liquid chromatography (LC). The LC may be reversed phase liquid chromatography (RPLC) with UV detection or LC linked with mass spectrometry (LC-MS). RPLC may be performed using an Agilent® HP1100, controlled with Agilent OpenLab, at 20° C. on a C18 Column, preferably a Phenomenex Luna ODS(3) 5 μm 100 Å 150×3 mm, with a 2×4 mm C18 guard column, using a mobile phase of acetonitrile (MeCN) in water ($H_2O$), both with 0.1 vol % formic acid. UV detection may be carried out at 206 nm, 262 nm, 348 nm and 382 nm and UV spectra recorded from 190 nm to 600 nm using Agilent® diode array detector. LC-MS may be performed on a Dionex Ultimate 3000 HPLC system at 20° C. on a C18 Column, preferably a Phenomenex Luna ODS(3) 5 μm 100 Å 150×3 mm, with a 2×4 mm C18 guard column, using a mobile phase of acetonitrile (MeCN) in water ($H_2O$), both with 0.1 vol % formic acid. MS detection may be obtained as positive ion mass spectra using an electrospray ionisation (ESI) source on a Bruker Micro-TOF-Q mass spectrometer linked to the Bionex Ultimate 3000 HPLC.

The genus *Dahlia* (Asteraceae) is best known for its various cultivated forms, which are often called *Dahlia variabilis*. A convenient naming convention for the various *Dahlia* varieties is *Dahlia* 'Variety name'. The native *Dahlia* species from Central and Southern America contain a wide variety of flavonoids, in different structural classes and as various glycoside conjugates. Extracts of any *Dahlia* variety may be used, including extracts of *Dahlia* 'Ruskin Diane', *Dahlia* 'Paroa glow', *Dahlia* 'Eastwood moonlight', *Dahlia* 'Megan', *Dahlia* 'Trengrove millennium', *Dahlia* 'Highward cliff' and *Dahlia* 'Hamari accord'.

The extracts may be formed from any part of the *Dahlia* plant comprising ILQ and/or BTN. It is not necessary for the plant part used to form the extract to comprise SLF as a portion of the BTN may be converted into SLF by oxidative cyclisation, which may be performed as a separate step or during the extraction process. Each of BTN, SLF and ILQ provides yellow pigmentation. The extract may be formed from any part of the *Dahlia* plant comprising yellow pigmentation. It has been found that BTN, SLF and ILQ are most concentrated in the petals of the *Dahlia* plant. Therefore, in some embodiments, the extract is formed from a petal of the *Dahlia* plant. *Dahlia* flowers include different types of petals (see FIGS. 14 and 15), with disc petals located in the centre of the flower and ray petals being positioned around the centre of the flower. Experiments have shown that the concentration of BTN, SLF and ILQ is substantially similar in all petal types. The extract may be prepared from any *Dahlia* petal, including a ray petal, a disc petal or a combination thereof. In some embodiments, the extract is formed from at least a ray petal of a *Dahlia* plant. Extraction of the ray petals is preferred as it allows for harvesting of the ray petals by "punching out" the central part of the flower (including disc petals). This harvesting technique reduces processing costs as it reduces the need to hand-pick the petals.

In some embodiments, the extract is formed from a whole flower of the *Dahlia* plant. In other embodiments, the extract is formed from a portion of the flower comprising at least a petal and one or more other parts of the flower, such as a stamen, a carpel and an ovary.

In some embodiments, the extract may be formed from a petal, and one or more other parts of the *Dahlia* plant which may be selected from the seeds, roots, leaves, stems, sepals, bulbs, tubers, a part thereof, or a combination thereof, or the extract may be formed from the whole plant. While it has been found that some parts of the *Dahlia* plant do not comprise significant quantities of BTN, SLF and/or ILQ, including the sepals, leaves and stems, these plant parts may be used to form the extract to avoid the costs associated with their removal prior to extraction.

The *Dahlia* plant may provide an extract comprising a relatively high concentration of BTN, SLF and ILQ making the extract a cost effective and a highly compatible resource of these active ingredients. It has been found that the concentration of BTN, SLF and ILQ present in a *Dahlia* plant may be dependent on a number of environmental factors received by the plant prior to harvesting, including UV exposure, total amount of light exposure per day (i.e. the photoperiod), air temperature, soil temperature, soil type and available nutrient concentrations. In some embodiments, the *Dahlia* plant used to form the extract has been exposed to environmental conditions similar to the conditions experienced in Southland, New Zealand.

As the highest concentration of BTN, SLF and/or ILQ may be found in the petals of the *Dahlia* plant, the extracts may be formed from the *Dahlia* plant when it is in a flowering stage of development. Extracts were analysed at different stages of the *Dahlia* plant's development. It was found that the concentration of the active ingredient(s) was highest when the plant was at or approaching full bloom, but where the central flower is not exposed and the flower had not reached reproductive maturity (see Example 4 and FIGS. 14-16). Accordingly, in some embodiments, the extract is formed from a *Dahlia* plant when the plant is at or approaching full bloom and before it has reached reproductive maturity.

The main flavonoids identified in extracts of *Dahlia* flowers include butein, isoliquiritigenin, sulfuretin, apigenin, luteolin, and derivatives thereof. In some embodiments, in addition to BTN, SLF and ILQ, the pharmaceutical compositions may comprise apigenin, a derivative thereof or a pharmaceutically acceptable salt thereof, and/or luteolin a derivative thereof or a pharmaceutically acceptable salt thereof.

References to butein, sulfuretin and isoliquiritigenin (and any other natural product) used herein include the relevant compound and pharmaceutically acceptable salts, tautomers, solvates and/or derivatives thereof.

The derivatives of these compounds include glycosides, diglycosides, malonates and methylated derivatives. These derivatives are typically formed on one or more of the phenol oxygen groups. Specific derivatives shown to be present in *Dahlia* extracts comprise butein 4'-O-β-glucopyranoside, isoliquiritigenin 4'-O-β-glucopyranoside and 4-methoxy butein. Such derivatives have been shown to be susceptible to hydrolysis and therefore it is appropriate to compare the total relative proportion of one compound and its derivatives to the amount of another compound for the pharmaceutical compositions of this invention. Accordingly, references to "BTN" include butein or a pharmaceutically acceptable salt, tautomer, solvate and/or derivative thereof; references to "SLF" include sulfuretin or a pharmaceutically acceptable salt, tautomer, solvate and/or derivative thereof; and references to "ILQ" include isoliquiritigenin or a pharmaceutically acceptable salt, tautomer, solvate and/or derivative thereof.

A "tautomer" is a structural isomer of a compound that is in equilibrium with another of the compound's structural isomers. This equilibrium is typically driven by thermodynamics making isolation of only one tautomer of a compound that exhibits tautomerism impossible by conventional techniques. To the extent that any of the present compounds exhibit tautomerism, it is intended that the invention includes all tautomers of the various compounds and derivatives thereof, including of BTN, SLF and ILQ.

The active ingredient(s) may exist in unsolvated as well as solvated forms with pharmaceutically acceptable solvents such as water, ethanol, and the like. The solvated forms of the active ingredient(s) are also considered to be disclosed herein. Solvates contain either stoichiometric or non-stoichiometric amounts of a solvent. Hydrates are formed when the solvent is water. Alcoholates are formed when the solvent is alcohol. In general, the solvated forms are considered equivalent to the unsolvated forms for the purposes of the pharmaceutical compositions and methods provided herein.

The active ingredient(s) may also be provided as salts which are pharmaceutically acceptable. Examples of pharmaceutically acceptable salts include salts of pharmaceutically acceptable cations such as sodium, potassium, lithium, calcium, magnesium, ammonium and alkylammonium. The salts may be formed by conventional means, such as by reacting one or more of the the phenol moieties of the flavonoids with one or more equivalents of an appropriate base, including inorganic and organic bases.

It should be understood that a reference to a pharmaceutically acceptable salt includes the solvent addition forms of the salt form of the relevant compound.

Figure 16:
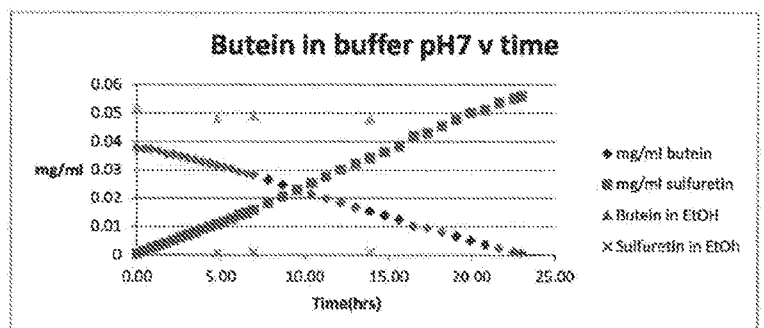
FIG. 16 shows a graph of RPLC analyses of a solution of butein in aqueous buffer at pH7 over time. This graph shows conversion of butein into sulfuretin.

Example 2 and FIG. 16 show that butein can be converted into sulfuretin under oxidative conditions when suspended in pH7 buffer and ethanol. This intramolecular cyclisation occurs when the phenol ortho to the carbonyl group on the phenyl ring of butein cyclises with the $sp^2$-hybridised alpha-carbon of the carbonyl group of butein forming the aurone 6,5-bicyclic ring of sulfuretin. FIG. 16 shows a linear (zero order kinetics) conversion of butein to sulfuretin over time when either ethanol (EtOH) or dimethylsulphoxide (DMSO) solutions of butein are diluted with aqueous buffer (pH7) at room temperature. Due to this observed cyclisation following extraction, in some embodiments, the amount of sulfuretin present in the extracts is a non-natural amount. The non-natural amount of sulfuretin may be obtained by conversion from butein. In addition, it is believed that the majority of the BTN and ILQ in the plant exist in the form of butein glycoside and isoliquiritigenin glycoside. Accordingly, in some embodiments, the pharmaceutical compositions comprise non-natural amounts of deglycosidated butein and/or deglycosidated isoliquiritigenin.

Extracts of the *Dahlia* plant may be prepared by any means known in the art. The pharmaceutical compositions of the extract will vary depending on the plant material selected, the plant variety, its growing conditions and the extraction method.

In some embodiments, the extract is formed by contacting one or more parts of the Dahlia plant with an extractant. Any suitable extractant known in the art may be used, including, for example, alcohols (e.g. methanol, ethanol, propanol, butanol, propylene glycol etc.), or a polar organic solvent (e.g. ethyl acetate, polyethylene glycol, dimethylsulphoxide, etc.), or a combination thereof. In some embodiments, the extractant may be combined with a carrier, such as water or a buffer (e.g. phosphate buffered saline). In some embodiments, the extract may be formed by contacting one or more parts of the Dahlia plant with an extractant comprising an alcohol, such as ethanol, and optionally one or more carriers, preferably water (e.g. in a ratio of 1:1 alcohol:water). The extractant is retained in contact with the plant material for a period of time sufficient to extract the desired compounds. In some embodiments, the extractant is maintained in contact with the plant material for at least about 0.5 hours, for example, 1, 2, 3, 4, 5, 6, 7, 8, 9, 10, 11, 12 hours or more. Experiments have shown that in the extraction of freeze dried petals obtained from Dahlia 'Ruskin Diane', the optimal extraction time was about 2 hours. It will be appreciated that the optimal extraction time may vary depending on various factors, including the nature of the plant material to be extracted (e.g. petals, whole flowers, etc), whether the plant material is fresh or dried, the extractant selected, and the extraction conditions. The extraction may be conducted at high temperature (e.g. greater than 50° C. and preferably not more than about 90° C. or about 70° C.), ambient temperature (e.g. about 20-25° C.) or at cold temperature (e.g. less than about 5° C.).

The extraction may be performed in the presence or absence of oxygen. For example, the extraction may be performed in the presence of oxygen, which is believed to assist in the conversion of BTN to SLF. Extraction excluding oxygen may be performed under an atmosphere of nitrogen with optional sparging of the extractant prior to contact with the plant material. In such embodiments, the extraction may further comprise the addition of SLF to the extract or exposing the extract to oxidising conditions to convert a portion of BTN to SLF. Suitable oxidising conditions include exposing the extract to oxygen in the presence of aqueous buffer (e.g. pH7 aqueous buffer) or adding an oxidant.

Extraction of the plant material in the presence of oxygen or including a step of adding an oxidant is carried out under oxidising conditions. Such conditions may assist in converting a portion of the BTN in the plant to SLF. Accordingly, also provided is a method of forming an extract of the Dahlia plant, comprising contacting at least a petal of a Dahlia plant with an extractant under oxidizing conditions.

The extractant may be completely or partially removed prior to incorporation of the Dahlia extract into the pharmaceutical compositions, or it may be included in the pharmaceutical compositions as a carrier. The extractant may be removed by heating the extract optionally under reduced pressure (e.g. under vacuum). It will be appreciated that some of the more volatile plant metabolites may also be removed with the extractant. Accordingly, in some embodiments, removing the extractant may enrich the concentration of secondary metabolites (e.g. flavonoids) in the extract. In some embodiments, the extract is filtered to remove particulate material, for example, by passing the extract through filter paper, a fine sieve or a screen (e.g. a sieve or screen with pore sizes of 5 µm or up to 0.5 mm depending on the size of the particulate material) and/or by centrifugation. Following removal of at least a portion of the extractant, the extract may be in the form of a powder, a film, an oil, a solution, a suspension, an emulsion or a colloid.

The one or more parts of the Dahlia plant used to form the extracts may be fresh or may be dried prior to extraction. Fresh plant material is preferably extracted within about 1 week of collection, for example, within about 6, 5, 4, 3, 2 or 1 day(s) of collection, or essentially immediately, e.g. within 1, 2, 3, 4, 5, 6, 12, or 24 hours of collection. The plant material, such as at least a petal of a Dahlia plant, may be dried by any suitable means known in the art, including freeze drying.

In some embodiments, one or more additional compounds (e.g. one or more of BTN, SLF and ILQ) may be added to the Dahlia extract. The addition of compounds may be to compensate for natural variations in the relative amounts of certain compounds being expressed in the Dahlia plant, or to supplement the relative amount of BTN and SLF and/or ILQ. The added compounds may be synthetic versions of the desired compounds (e.g. BTN, SLF and/or ILQ), they may be purified compounds obtained from other plant extracts, including other Dahlia extracts, or they may be added by blending two or more Dahlia extracts.

In some embodiments, specific flavonoids may be absent, or present in non-detectable amounts (e.g. less than about 0.001% by weight of the analyte).

The amounts of BTN, SLF, ILQ and other flavonoid compounds identified in some extracts of Dahlia plants are described in Table 2. The extracts described in Table 2 were obtained by contacting flowers from the various Dahlia plants with ethanol (about 3 parts EtOH to 1 part plant material).

TABLE 2

Amounts of BTN, SLF, ILQ and other flavonoid compounds in extracts of various Dahlia plants

| Compound name | Conc. in extract of Dahlia 'Paroa Glow' (mg/ml) | Conc. in extract of Dahlia 'Ruskin Diane' (mg/ml) | Conc. in extract of Dahlia 'Eastwood moonlight'-1[a] (mg/ml) | Conc. in extract of Dahlia 'Eastwood moonlight'-2[b] (mg/ml) | Conc. in extract of Dahlia 'Megan' (mg/ml) | Conc. in extract of Dahlia 'Trengrove millenium' (mg/ml) | Conc. in extract of Dahlia (Highwarden cliff) (mg/ml) | Conc. in extract of Dahlia (Hamari accord)[c] (mg/ml) |
|---|---|---|---|---|---|---|---|---|
| Butein glycoside | 0.14 | 0.01 | 0.02 | 0.01 | 0.04 | 0.01 | 0.02 | 0.20 |
| Isoliquiritigenin glycoside | 0.07 | 0.03 | 0.04 | 0.03 | 0.08 | 0.01 | 0.01 | 0.26 |
| Sulfuretin | 0.47 | 0.71 | 0.41 | 0.29 | 0.79 | 0.44 | 0.37 | 0.06 |
| Luteolin | 0.82 | 0.12 | 0.12 | 0.07 | 0.06 | 0.17 | 0.10 | 0.03 |

TABLE 2-continued

Amounts of BTN, SLF, ILQ and other flavonoid compounds in extracts of various *Dahlia* plants

| Compound name | Conc. in extract of *Dahlia* 'Paroa Glow' (mg/ml) | Conc. in extract of *Dahlia* 'Ruskin Diane' (mg/ml) | Conc. in extract of *Dahlia* 'Eastwood moonlight'-1[a] (mg/ml) | Conc. in extract of *Dahlia* 'Eastwood moonlight'-2[b] (mg/ml) | Conc. in extract of *Dahlia* 'Megan' (mg/ml) | Conc. in extract of *Dahlia* 'Trengrove millenium' (mg/ml) | Conc. in extract of *Dahlia* (Highwarden cliff) (mg/ml) | Conc. in extract of *Dahlia* (Hamari accord)[c] (mg/ml) |
|---|---|---|---|---|---|---|---|---|
| Butein | 0.11 | 0.36 | 0.18 | 0.02 | 0.27 | 0.07 | 0.13 | 0.01 |
| Apigenin | 0.26 | 1.22 | 0.95 | 0.05 | 0.44 | 1.64 | 0.76 | 0.05 |
| Isoliquiritigenin | 0.12 | 0.48 | 0.23 | 0.03 | 0.29 | 0.26 | 0.19 | 0.02 |
| 4-O-methyl-butein | 0.15 | 0.18 | 0.09 | 0.01 | 0.01 | 0.16 | 0.07 | 0.01 |

Notes:
[a]extractant separated from plant material and stored at −18° C.;
[b]plant material kept in contact with extractant; [c]extract obtained from freeze dried flowers.

Methods of Treatment

The inventors have surprisingly found that the combinations of BTN and ILQ, BTN and SLF and BTN, ILQ and SLF are able to treat impairment of glucose regulation. The positive effects of these combinations were surprising in particular as not every combination of the active ingredients possessed the same efficacy, notably treatment with the combination of SLF and ILQ in the absence of BTN lacked sufficient efficacy. The reversal of diet-induced impairment of glucose regulation suggests that treatment with the active combinations is able to positively impact glucose homeostasis by at least partially restoring glucose tolerance and/or insulin sensitivity. Accordingly, the active combinations may be useful in the treatment of diabetes and associated diseases, conditions and/or disorders.

The present invention provides methods of treating diabetes and associated diseases, conditions and/or disorders, comprising administering to a subject in need thereof an effective amount of a pharmaceutical composition comprising BTN and SLF and/or ILQ. In these methods, the pharmaceutical compositions may comprise BTN and SLF and/or ILQ in any ratio. Any pharmaceutical compositions comprising BTN and at least one of SLF and/or ILQ described herein may be used in these methods.

The methods may treat any form of diabetes, including type 1 diabetes, type 2 diabetes and gestational diabetes.

Diseases, conditions and/or disorders associated with diabetes include any disease, condition and/or disorder linked to diabetes, symptoms thereof, complications thereof or diabetes' underlying causes, such as impairment of the regulation of glucose in vivo and/or insulin resistance. These diseases, conditions and/or disorders include prediabetes, glycosuria, hyperglycemia, hyperinsulinemia, insulin resistance, and combinations thereof. In some embodiments, the methods may result in a reduction of plasma glucose concentration for a period of time following treatment. The plasma glucose concentration following administration of the composition may be reduced by at least about 1%, 2%, 3%, 4%, 5%, 6%, 7%, 8% or more relative to a baseline plasma glucose concentration determined by a standard oral glucose tolerance test (OGTT—see Example 6 for test procedure). The period of time following treatment may be at least about 30 minutes, 60 minutes, 90 minutes, 120 minutes, 180 minutes, 240 minutes, 300 minutes or longer. In some embodiments, the plasma glucose concentration is reduced without significantly affecting the insulin and/or C-peptide concentration(s). In some embodiments, the insulin and/or C-peptide concentration(s) are not significantly reduced by administration of the pharmaceutical composition. The concentration of insulin or C-peptide is considered to be significantly affected (e.g. reduced) if the variation in concentration following treatment differs from the concentration prior to treatment by a statistically significant amount, for example, determined by ANOVA. C-peptide is excised from proinsulin during insulin biosynthesis. C-peptide concentration may be useful in the diagnosis of type of diabetes, and its plasma concentration correlates to insulin production in B-cells.

In some embodiments, the invention provides a method of treating diabetes and/or prediabetes. In some embodiments, the invention provides a method of treating prediabetes preferably so that the prediabetes does not progress to diabetes.

Prediabetes typically relates to a state of abnormally regulated blood glucose levels which may progress to diabetes if left untreated. In some instances, prediabetes relates to a condition defined as having blood glucose levels above normal but below the defined threshold of diabetes. Prediabetes has been defined by the World Health Organisation as being a state of intermediate hyperglycemia which is defined by two criteria: (1) impaired fasting glucose (IFG) and (2) impaired glucose tolerance (IGT). The American Diabetes Association also defines prediabetes in terms of IFG and IGT and includes additional haemoglobin A1c (HbA1c) based criteria. The definition, diagnosis and treatment of prediabetes is discussed in Bansal, N. *World J Diabetes* 2015; 6(2): 296-303, the contents of which are entirely incorporated herein by reference. In some embodiments, a subject is in need of treatment for diabetes and associated diseases, conditions and/or disorders if their HbA1c levels are from about 41 mmol/mol to about 60 mmol/mol. Typically, subjects with HbA1c levels from about 41 to about 49 mmol/mol are considered to be in need of treatment for prediabetes.

In some embodiments, the invention provides a method of returning glucose metabolism to normal.

In some embodiments, the invention provides a method of treating impairment of glucose regulation, including diet-induced impairment of glucose regulation.

Diabetes and associated diseases, conditions and/or disorders are linked to certain complications. For example, known complications of diabetes include diabetes associated inflammation, diabetic retinopathy, diabetic nephrology and diabetic neuropathy. While the present invention relates to the treatment of diabetes and associated diseases, conditions and/or disorders and not the complications of these diseases, conditions and/or disorders, the complications may be avoided, reduced in severity or their onset delayed by treating diabetes or an associated disease, condition and/or disorder.

The methods involve administering an effective amount of BTN and SLF and/or ILQ. The effective amount may be determined by the skilled person based on numerous factors, including the severity and kind of symptoms of the subject, the subject's medical history, the subject's physical attributes (weight, sex, etc), the specific combination of active ingredients included in the pharmaceutical compositions to be administered and the administration route.

In some embodiments, the effective amount of the combination of BTN and SLF and/or ILQ may be at least about 0.001 mg/kg, for example, the effective amount of the combination of BTN and SLF and/or ILQ may be an amount sufficient to administer to the subject at least about 0.01 mg/kg, about 0.1 mg/kg, about 0.3 mg/kg, about 0.33 mg/kg, about 1 mg/kg, about 1.5 mg/kg, about 3 mg/kg, about 3.3 mg/kg, about 5 mg/kg or about 10 mg/kg. In some embodiments, the effective amount of the combination of BTN and SLF and/or ILQ may be from about 0.001 mg/kg to about 50 mg/kg, for example, from about 0.001 mg/kg to about 20 mg/kg, from about 0.01 mg/kg to about 10 mg/kg or from about 0.05 mg/kg to about 5 mg/kg. In some embodiments, the effective amount of the combination of BTN and SLF and/or ILQ may be at least about 0.5 mg/m$^2$, about 0.6 mg/m$^2$, 0.7 mg/m$^2$, 0.8 mg/m$^2$, 0.9 mg/m$^2$, 1.0 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2.0 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3.0 mg/m$^2$, 3.5 mg/m$^2$, 4.0 mg/m$^2$, 4.5 mg/m$^2$, 5.0 mg/m$^2$, 5.5 mg/m$^2$, 5.6 mg/m$^2$, 5.7 mg/m$^2$, 5.8 mg/m$^2$, 5.9 mg/m$^2$, 6.0 mg/m$^2$, 7.0 mg/m$^2$, 8.0 mg/m$^2$, 9.0 mg/m$^2$, 10 mg/m$^2$, or more. The effective amount of the combination of BTN and SLF and/or ILQ may be between any of these doses, for example, from about 0.5 mg/m$^2$ to about 10 mg/m$^2$ or about 1.5 mg/m$^2$ to about 6.0 mg/m$^2$.

The effective amount of BTN may be at least about 0.001 mg/kg, for example, the effective amount of BTN may be an amount sufficient to administer to the subject at least about 0.01 mg/kg, about 0.1 mg/kg, about 0.3 mg/kg, about 0.33 mg/kg, about 1 mg/kg, about 3 mg/kg, about 3.3 mg/kg, about 5 mg/kg or about 10 mg/kg. In some embodiments, the effective amount of BTN may be from about 0.001 mg/kg to about 50 mg/kg, for example, from about 0.001 mg/kg to about 20 mg/kg, from about 0.01 mg/kg to about 10 mg/kg or from about 0.01 mg/kg to about 5 mg/kg. In some embodiments, the effective amount of BTN may be at least about 0.1 mg/m$^2$, for example, at least about 0.2 mg/m$^2$, about 0.3 mg/m$^2$, about 0.4 mg/m$^2$, about 0.5 mg/m$^2$, about 0.6 mg/m$^2$, 0.7 mg/m$^2$, 0.8 mg/m$^2$, 0.9 mg/m$^2$, 1.0 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2.0 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3.0 mg/m$^2$, 3.5 mg/m$^2$, 4.0 mg/m$^2$, 4.5 mg/m$^2$, 5.0 mg/m$^2$, 5.5 mg/m$^2$, 5.6 mg/m$^2$, 5.7 mg/m$^2$, 5.8 mg/m$^2$, 5.9 mg/m$^2$, 6.0 mg/m$^2$ or more. The effective amount of BTN may be between any of these doses, for example, from about 0.1 mg/m$^2$ to about 6 mg/m$^2$ or about 2.0 mg/m$^2$ to about 4.0 mg/m$^2$.

The effective amount of SLF may be at least about 0.001 mg/kg, for example, the effective amount of SLF may be an amount sufficient to administer to the subject at least about 0.01 mg/kg, about 0.1 mg/kg, about 0.3 mg/kg, about 0.33 mg/kg, about 1 mg/kg, about 3 mg/kg, about 3.3 mg/kg, about 5 mg/kg or about 10 mg/kg. In some embodiments, the effective amount of SLF may be from about 0.001 mg/kg to about 50 mg/kg, for example, from about 0.001 mg/kg to about 20 mg/kg, from about 0.01 mg/kg to about 10 mg/kg or from about 0.01 mg/kg to about 5 mg/kg. In some embodiments, the effective amount of SLF may be at least about 0.1 mg/m$^2$, for example, at least about 0.2 mg/m$^2$, about 0.3 mg/m$^2$, about 0.4 mg/m$^2$, about 0.5 mg/m$^2$, about 0.6 mg/m$^2$, 0.7 mg/m$^2$, 0.8 mg/m$^2$, 0.9 mg/m$^2$, 1.0 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2.0 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3.0 mg/m$^2$, 3.5 mg/m$^2$, 4.0 mg/m$^2$ or more. The effective amount of SLF may be between any of these doses, for example, from about 0.1 mg/m$^2$ to about 4 mg/m$^2$ or about 1.0 mg/m$^2$ to about 2.0 mg/m$^2$.

The effective amount of ILQ may be at least about 0.001 mg/kg, for example, the effective amount of ILQ may be an amount sufficient to administer to the subject at least about 0.01 mg/kg, about 0.1 mg/kg, about 0.3 mg/kg, about 0.33 mg/kg, about 1 mg/kg, about 3 mg/kg, about 3.3 mg/kg, about 5 mg/kg or about 10 mg/kg. In some embodiments, the effective amount of ILQ may be from about 0.001 mg/kg to about 50 mg/kg, for example, from about 0.001 mg/kg to about 20 mg/kg, from about 0.01 mg/kg to about 10 mg/kg or from about 0.01 mg/kg to about 5 mg/kg. In some embodiments, the effective amount of ILQ may be at least about 0.1 mg/m$^2$, for example, at least about 0.2 mg/m$^2$, about 0.3 mg/m$^2$, about 0.4 mg/m$^2$, about 0.5 mg/m$^2$, about 0.6 mg/m$^2$, 0.7 mg/m$^2$, 0.8 mg/m$^2$, 0.9 mg/m$^2$, 1.0 mg/m$^2$, 1.1 mg/m$^2$, 1.2 mg/m$^2$, 1.3 mg/m$^2$, 1.4 mg/m$^2$, 1.5 mg/m$^2$, 1.6 mg/m$^2$, 1.7 mg/m$^2$, 1.8 mg/m$^2$, 1.9 mg/m$^2$, 2.0 mg/m$^2$, 2.1 mg/m$^2$, 2.2 mg/m$^2$, 2.3 mg/m$^2$, 2.4 mg/m$^2$, 2.5 mg/m$^2$, 2.6 mg/m$^2$, 2.7 mg/m$^2$, 2.8 mg/m$^2$, 2.9 mg/m$^2$, 3.0 mg/m$^2$, 3.5 mg/m$^2$, 4.0 mg/m$^2$ or more. The effective amount of ILQ may be between any of these doses, for example, from about 0.1 mg/m$^2$ to about 4 mg/m$^2$ or about 1.2 mg/m$^2$ to about 2.3 mg/m$^2$.

In embodiments where the combination of BTN and SLF and/or ILQ are provided in the form of a *Dahlia* extract, the method may comprise administering an effective amount of the *Dahlia* extract to the subject. In some embodiments, the effective amount of the extract may be at least about 5 mg/m$^2$, for example, at least about 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, 95 mg/m$^2$, 100 mg/m$^2$, or more. The effective amount of the extract may be between any of these doses, for example, from about 5 mg/m$^2$ to about 100 mg/m$^2$ or about 55 mg/m$^2$ to about 65 mg/m$^2$.

In some embodiments, the effective amount relates to a hormetic amount of the pharmaceutical compositions and/or the active ingredients. Hormesis refers to a biphasic dose response to an active ingredient which typically involves beneficial activity of the active ingredient at a low dose and either a loss of activity or deleterious activity at a high dose. Hormesis is described in Mattson, M. P. *Ageing Res Rev.* 2008; 7(1): 1-7, the contents of which are entirely incorporated herein by reference. Some embodiments of the pharmaceutical compositions of the present invention demonstrated hormesis in that their efficacy was shown to be greater at low doses, for example, a pharmaceutical composition comprising 1:1:1 SLF:ILQ:BTN showed a striking reversal of diet-induced impairment of glucose regulation when administered at about 1 mg/kg (see Example 1; Experiment 4 and FIG. 4).

The method may also comprise administering an active ingredient other than BTN, SLF and/or ILQ. This active ingredient may be administered simultaneously, separately or consecutively with the BTN and SLF and/or ILQ. By simultaneously it is meant that each of the pharmaceutical composition and the other active ingredient are administered at the same time in the same pharmaceutical composition. By separately it is meant that each of the pharmaceutical composition and the other active ingredient are administered at the same time in different pharmaceutical compositions and optionally by different routes of administration. By consecutively it is meant that each of the pharmaceutical composition and the other active ingredient are administered separately optionally by different administration routes and may be at different times. Typically, when the pharmaceutical composition and the other active ingredient are administered consecutively they are administered within 24 hours, or within 12, 8, 6, 5, 4, 3, 2, or 1 hour(s) of each other. The pharmaceutical composition may be administered before or after the other active ingredient. Further, the route of administration for the pharmaceutical composition and the other active ingredient may be the same or different.

In embodiments, the other active ingredient may be any existing therapy for diabetes, such as administration of a biguanide (such as metformin), a dipeptidyl peptidase 4 (DPP-IV) inhibitor (such as sitagliptin, saxagliptin, vidagliptin, linagliptin and alogliptin), a sodium-glucose cotransporter (SGLT2) inhibitor (such as canagliflozin, dapaglifozin and empagliflozin), an insulin (such as Short-acting Regular Insulin (e.g. Humulin, Novolin), Intermediate NPH Insulin, Long-acting Insulin glargine (e.g. Lantus), Insulin detemir (e.g. Levemir), Insulin degludec (e.g. Tresiba), Rapid-acting Humalog (e.g. Lispro), Novolog (e.g. Aspart), Glulisine (e.g. Apidra), Pre-mixed 75% insulin lispro protamine/25% insulin lispro (e.g. Humalog Mix 75/25), 50% insulin lispro protamine/50% insulin lispro (e.g. Humalog Mix 50/50), 70% insulin lispro protamine/30% insulin aspart (e.g. Novolog 70/30), 70% NPH insulin/30% regular), GLP-1 agonists (such as liraglutide, exenatide and dulaglutide), a sulfonylurea (SU) (such as glimepiride, glipizide and glyburide), a thiazolidinedione (TZD) (such as rosiglitazone and pioglitazone), an amylin agonist (such as pramlintide), an alpha glucosidase inhibitor (such as acarbose) and combinations thereof. Additional information relating to suitable other active ingredients is described in Chaundry, A., et al. *Frontiers in Endocrinology*, 2017; 8:Article 6, the contents of which is entirely incorporated herein by reference.

In some embodiments, the method comprises administering the pharmaceutical composition and an amylin agonist, such as pramlintide. The inventors have observed synergism in terms of efficacy against diet-induced impairment of glucose regulation in embodiments comprising administration of an amylin agonist and the pharmaceutical composition (see Example 1; Experiment 8). Accordingly, in some embodiments, the method comprises administering a synergistic amount of the pharmaceutical composition and an amylin agonist, such as pramlintide. In some embodiments, the method comprises administering the pharmaceutical composition in an amount sufficient to administer to the subject from about 0.01 mg/kg to about 10 mg/kg or about 0.1 mg/m² to about 4.0 mg/m² of each active ingredient in the pharmaceutical composition, together with the amylin agonist, such as pramlintide. The method may comprise administering a pharmaceutical composition comprising the combination of BTN and SLF and/or ILQ together with the amylin agonist, such as pramlintide. In embodiments where the amylin agonist is pramlintide, the method may comprise administering pramlintide in an amount less than that required to observe efficacy by itself. By administering subclinical doses of pramlintide, associated side-effects may be reduced or avoided. The method may comprise administering pramlintide in an amount sufficient to administer to the subject up to about 1000 mg/kg, for example, up to about 500 mg/kg, 400 mg/kg, 300 mg/kg, 200 mg/kg or a lower amount.

The method may comprise any suitable route of administration, including any administration route described herein.

In another aspect, the invention provides a kit comprising in separate parts:
(a) butein or a pharmaceutically acceptable salt, tautomer, solvate and/or derivative thereof (BTN); and
(b) sulfuretin or a pharmaceutically acceptable salt, tautomer, solvate and/or derivative thereof (SLF); and/or
(c) isoliquiritigenin or a pharmaceutically acceptable salt, tautomer, solvate and/or derivative thereof (ILQ).

In some embodiments, part (b) or (c) is absent.

In some embodiments, part (a) of the kit further comprises SLF and/or ILQ. In some embodiments, part (b) of the kit further comprises BTN and/or ILQ. In some embodiments, part (c) of the kit further comprises BTN and/or SLF.

In some embodiments, one or more of parts (a), (b) and/or (c) of the kit independently further comprises a pharmaceutically acceptable excipient. In other embodiments, the pharmaceutically acceptable excipient is provided in a further part of the kit, namely part (d).

In some embodiments, the kit may comprise in a separate part (e) an active ingredient other than BTN, SLF and/or ILQ. Part (e) may be included in the kit, in addition to parts (a), (b), (c) and/or (d).

In some embodiments, the kit may comprise in a separate part (f) instructions for use for treating diabetes or an associated disease, condition and/or disorder.

Figure 3:
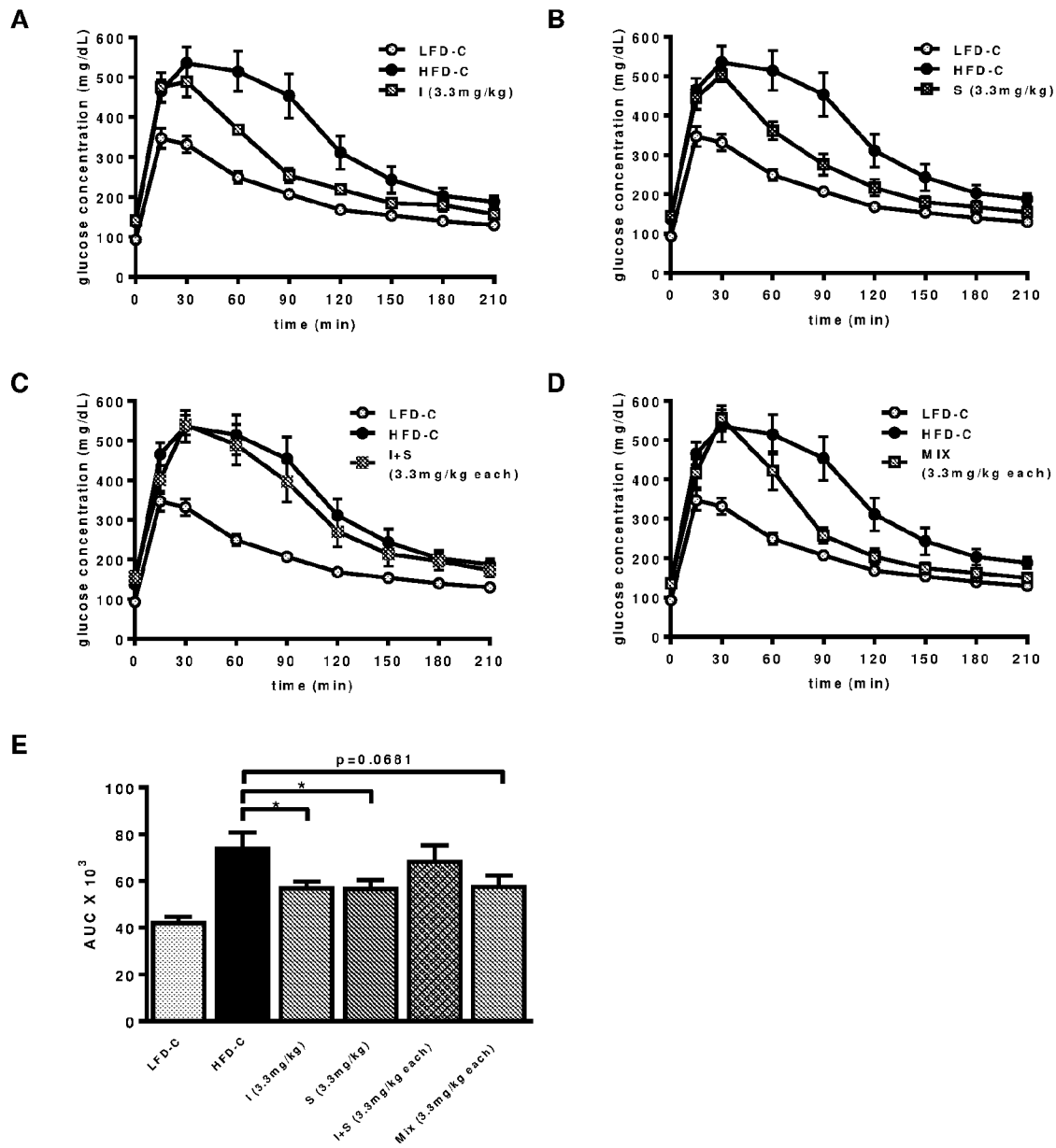
FIGS. 3A-D show graphs of ipGTT results on C57BL/6 mice fed (1) a high fat diet (HFD) for 4 weeks; (2) a low fat diet (LFD) for 4 weeks or (3) a high fat diet for 4 weeks and followed by treatment with isoliquiritigenin (A), sulfuretin (S), a 1:1 combination of isoliquiritigenin and sulfuretin (C) and a 1:1:1 mixture of butein, sulfuretin and isoliquiritigenin (D).
FIG. 3E shows a bar graph comparing the area under the curve for the ipGTT results shown in FIGS. 3A-D.

The inventors have shown that isoliquiritigenin alone is able to treat diet-induced impairment of glucose regulation (Example 1; Experiment 1, FIG. 1B; Experiment 3, FIG. 3A).

Accordingly, in another aspect, the invention provides methods of treating diabetes and associated diseases, conditions and/or disorders, comprising administering to a subject in need thereof an effective amount of isoliquiritigenin or a pharmaceutically acceptable salt, tautomer, solvate and/or derivative thereof (ILQ). These methods may be used in the treatment of any form or diabetes and any associated diseases, conditions and/or disorders as described herein.

Also provided is the use of ILQ in the preparation of a medicament for treating diabetes and associated diseases, conditions and/or disorders.

Also provided are pharmaceutical compositions for use in treating diabetes and associated diseases, conditions and/or disorders, wherein the pharmaceutical composition comprises ILQ.

Also provided is an antidiabetic agent comprising ILQ.

ILQ may be administered in any form described herein alone (i.e. as the sole active ingredient) or in combination with BTN, SLF and/or an active ingredient other than SLF, BTN and/or ILQ. Pharmaceutical compositions comprising ILQ may comprise ILQ in any amount described herein. ILQ may be obtained from any source described herein, including forms of ILQ that are synthetic or semi-synthetic in origin.

Figure 17:
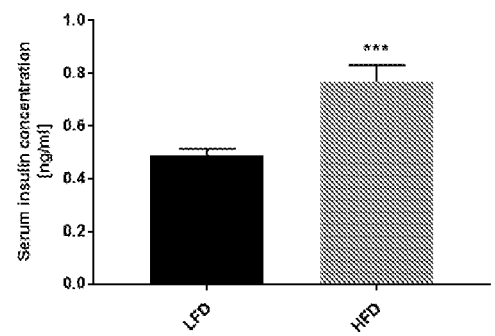
FIG. 17 shows a graph comparing insulin levels in mice on either LFD or HFD for 4 weeks as measured by commercially available ELISA (n=33/group).

The inventors have surprisingly found that treatment with sulfuretin alone is able to treat diet-induced impairment of glucose regulation. Previously, it was shown that sulfuretin was capable of blocking cytokine-induced beta cell damage. However, the inventors have shown that the efficacy of sulfuretin is independent of beta cell damage as the mice on HFD were hyperinsulinemic (see Example 3 and FIG. 17). Example 1 shows that sulfuretin is able to treat impairment of glucose regulation that was induced by diet during states of hyperinsulinemia prior to beta cell failure. It was therefore surprising that SLF possesses efficacy in the treatment of diet-induced insulin resistance and impairment of glucose regulation independent of beta cell failure, including type 2 diabetes and prediabetes.

Accordingly, provided herein are methods of treating type 2 diabetes, prediabetes and/or diet-induced impairment of glucose regulation, comprising administering to a subject in need thereof an effective amount of SLF.

Also provided is the use of SLF in the preparation of a medicament for treating type 2 diabetes, prediabetes and/or diet-induced impairment of glucose regulation.

Also provided are pharmaceutical compositions for use in treating type 2 diabetes, prediabetes and/or diet-induced impairment of glucose regulation, wherein the pharmaceutical composition comprises SLF.

Also provided is an anti-type 2 diabetes and/or prediabetes agent comprising SLF.

SLF may be administered in any form described herein alone (i.e. as the sole active ingredient) or in combination with BTN, ILQ and/or an active ingredient other than SLF, BTN and/or ILQ. Pharmaceutical compositions comprising SLF may comprise SLF in any amount described herein. SLF may be obtained from any source described herein, including forms of SLF that are synthetic or semi-synthetic in origin.

EXAMPLE(S)

The invention will be further described by way of non-limiting example(s). It will be understood to persons skilled in the art of the invention that many modifications may be made without departing from the spirit and scope of the invention.

Example 1: Experiments 1 to 10

This Example describes a series of experiments showing the efficacy of BTN, SLF and/or ILQ in reversing diet-induced glucose sensitivity in mice. The mice used are considered a model for human diabetes and prediabetes. For the purposes of this Example, the abbreviations set out in Table 3 will be used.

TABLE 3

| Abbreviations | |
| --- | --- |
| Term | Abbreviation |
| Butein | B |
| Isoliquiritigenin | I |
| Sulfuretin | S |
| 1:1:1 by weight combination of B, I and S | mix |
| Ethanol | EtOH |
| Dimethylsulphoxide | DMSO |

TABLE 3-continued

| Abbreviations | |
| --- | --- |
| Term | Abbreviation |
| High-fat diet containing 60% fat; cat. No. D12492; Research Diets | HFD |
| Low-fat diet containing 10% fat; cat. no. D12450B; Research Diets | LFD |
| intraperitoneal glucose tolerance test | ipGTT |
| Phosphate buffered saline | PBS |
| Area under the curve | AUC |
| Hour | h |
| Diet-induced obese | DIO |
| Protein kinase B | AKT |
| Phosphorylated protein kinase B | pAKT |
| Hematoxylin and eosin stain | H&E Stain |
| Glial fibrillary acidic protein | GFAP |
| Arcuate nucleus of the hypothalamus | ARC |

Experimental

Animals

For all experiments, 12-14 weeks old male C57BL/6 mice were obtained from the University of Otago animal facility. All procedures were approved by the University of Otago Animal Ethics Committee. Mice were housed individually under a 12:12 h light/dark cycle and ambient temperature was 23° C. Animals had either access to low-fat diet (LFD, containing 10% fat; cat. no. D12450B; Research Diets) or high-fat diet (HFD, containing 60% fat; cat. No. D12492; Research Diets) for a duration of 4 weeks, and water ad libitum. For each experiment a new cohort of animals was employed.

Formulation

For all experiments, the formulations were prepared by forming an ethanol solution of the selected active ingredient(s), i.e. B, I or S individually, the mix or the extract, and then diluting to the desired concentration with 0.9 wt % NaCl aqueous solution.

A general example for preparing a representative formulation is as follows. To the active ingredient (10 mg) was added 500 µl ethanol followed by 9500 µl 0.9 wt % NaCl aqueous solution to make up a 10 ml solution for administration.

Formulations of combinations of two or more active ingredients may be prepared by pre-weighing the two or more active ingredients, adding 5 parts ethanol followed by 95 parts of a 0.9% NaCl aqueous solution. Alternatively, the formulation may be prepared by taking an aliquot from an already prepared solution of one active ingredient (e.g. prepared in the manner described above) and combining with a solution of the other active ingredient(s) of the combination.

Extract

For all experiments, the extract was prepared by contacting fresh intact petals (1 part) obtained from *Dahlia* 'Ruskin Diane' with 96% ethanol (about 3 parts). Extracts were stored as ethanol solutions at −18° C. until required. The amounts of flavonoids found by RPLC analysis in this extract are set out below in Table 4.

TABLE 4

Amounts of B, S, I and other flavonoid compounds in an extract of *Dahlia* 'Ruskin Diane'

| Compound name | Conc. in extract of *Dahlia* 'Ruskin Diane' (mg/ml) |
|---|---|
| Butein | 0.36 |
| Butein glycoside | 0.01 |
| 4-O-Methyl-butein | 0.18 |
| Sulfuretin | 0.71 |
| Isoliquiritigenin | 0.48 |
| Isoliquiritigenin glycoside | 0.03 |
| Luteolin | 0.12 |
| Apigenin | 1.22 |

Glucose Tolerance Test

Experiments 1-3: Antidiabetic Properties of Compounds

To investigate whether the compounds either individually, a mixture of all three compounds (B, S and I; hereinafter referred to as "mix") or the total extract of yellow *Dahlia* 'Ruskin Diane' petals acutely affect glucose homeostasis, intraperitoneal glucose tolerance tests (ipGTTs) were performed in diet-induced obese (DIO) mice as a model to mimic human prediabetes and impairments in glucose metabolism. Individual compounds, the mix or the total extract were dissolved in 0.9% NaCl containing 5% ethanol and administered orally. Mice (n=7-8/group) were fed either a high fat diet (HFD) or respective low fat diet (LFD) for 4 weeks, fasted for 16 h and received the different compounds/combinations or vehicle (0.9% NaCl containing 5% ethanol) by oral gavage. For example, for administration to a 50 g mouse, an oral gavage having a volume of 500 µl was prepared, the oral gavage contained 500 µg of extract or 50 µg of compound(s). The volume of the gavage administered was adjusted based on the weight of the mouse subject. Glucose (1.5 g/kg body weight; dissolved in 0.9% NaCl) was injected intraperitoneally (i.p.) 60 minutes after oral gavage treatment, and an ipGTT was performed. Blood glucose levels were measured using a commercially available glucometer (Accu-Check Performa; Roche) whilst truncating the tip of the tail with a fresh scalpel blade. For statistical validation, the area under the curve (AUC) was calculated.

Experiments 4-5: Dose Response of Mix and Extract

These experiments establish dose responses of the individual compounds using different concentrations (20, 10, 3.3, 1, 0.33 mg/kg body weight), the mix (20, 10, 3.3, 1, 0.33 mg/kg body weight) or the extract (50, 20, 10, 3.3, 1 mg/kg) to determine the highest non-effective dose to allow for testing of synergism in combination with commercially available diabetes drugs in subsequent experiments. Mice were fed either LFD or HFD 4 weeks (Experiments 4 and 5). After mice were food deprived for 16 hours, an pGTT was carried out as previously described.

Experiments 6 and 8: Dose Response of Metformin and Pramlintide

To analyse whether B and S and/or I act in synergy with the well described diabetes drugs metformin and pramlintide to affect glucose homeostasis, a dose response experiment for these two agents was conducted. Mice were fed a HFD or a LFD for 4 weeks and treated chronically with metformin (oral gavage for last 7 days, twice daily (12 hours apart); 300, 100, 50, 20, 10 mg/kg/d in PBS) or pramlintide (subcutaneous injection for last 5 days, twice daily (12 hours apart); 1000, 200, 40, 8, 1.6 µg/kg/d in 0.9% NaCl). Separate cohorts of mice were treated with the respective control injections. Mice were fasted for 16 h and an ipGTT was performed as described.

Experiments 7 and 9: Combination with Metformin and Pramlintide

Having established a dose response for the diabetes agents and our compounds, in this experiment the highest non-effective dose of metformin or pramlintide was chosen and administered in combination with the highest non-effective dose of the mix to test for synergistic effects on improving glucose homeostasis. Therefore, mice were fed either a HFD or LFD for 4 weeks and treated with metformin (oral gavage for last 7 days, twice daily (12 hours apart); 100 mg/kg/d body weight in PBS) or pramlintide (subcutaneous injection for last 5 days, twice daily (12 hours apart); 200 µg/kg/d body weight in 0.9% NaCl). After chronic treatment with the well described antidiabetic drugs mice were fasted for 16 h and received the mix acutely (0.33 mg/kg; containing 5% ethanol). 60 minutes later we carried out an ipGTT as described previously.

Experiment 10: Effects on Central Insulin Signalling

To identify a mode of action of how the compounds, formulations and the extract affect glucose homeostasis, effects on central insulin signalling by measuring phosphorylation of AKT (pAKT) were investigated. AKT is the main target of insulin in the arcuate nucleus of the hypothalamus. To assess the degree of insulin action in the hypothalamus, phosphorylated AKT positive cells were counted. Mice were fed LFD or HFD for 4 weeks, fasted for 16 h and body-weight matched. Sixty minutes before transcardial perfusion they received B (10 mg/kg), I (10 mg/kg), S (10 mg/kg), the mix (3.3 mg/kg of each compound), the extract (10 mg/kg) or vehicle (0.9% NaCl containing 5% ethanol) by oral gavage. Additionally, mice received an insulin (1 mg/kg) or vehicle injection 15 minutes before transcardial perfusion. Immunohistochemistry was carried out on mouse brain coronal cryosections as described previously in Benzler J, et al. *Diabetes*. 2015; 64:2015-27 the contents of which are entirely incorporated herein by reference, using an anti-phospho-AKT Ser473 antibody (cat. no. 4058; Cell Signaling Technology).

Statistics

Data were analysed by one-way ANOVA or repeated measures ANOVA followed by multiple comparison test, as appropriate, using GraphPad Prism 5 software (Graphpad Software, Inc.). The results are presented as means ±SEM, and differences were considered significant if $p \leq 0.05$.

Results

Experiment 1: Antidiabetic Properties of Compounds

Experiment 1: First Proof of Antidiabetic Properties of Extract and Certain Compounds C57BL/6 mice were fed a HFD or LFD for 4 weeks and received B, I, S, a mix of all three or an extract of *Dahlia* petals at 10 mg/kg (diluted in 0.9% NaCl/5% ethanol) orally 1 h before an ipGTT was performed (n=6-7/group). S, the mix and the extract significantly improved glucose tolerance.

In this experiment, improvement of glucose homeostasis in HFD-fed mice was investigated for the compounds either individually (10 mg/kg), as a mix of all three compounds (3.3 mg/kg of each compound) or as a whole extract of *Dahlia* petals (10 mg/kg). After 4 weeks of feeding the diets, as expected glucose tolerance was significantly impaired in the HFD group compared to the LFD group (p<0.0001). Given acutely by oral gavage one hour before the ipGTT, S (p=0.027), the mix (p=0.0013) and the extract (p=0.0081) were able to significantly improve glucose tolerance, while I showed a trend towards an improved glucose homeostasis compared with the control group (FIG. 1) (p=0.10). B did not improve glucose tolerance at either time-point throughout the ipGTT. These data suggest that at these tested doses S, the mix and the *Dahlia* extract are effective agents to improve glucose homeostasis in diet-induced obese (DIO) mice.

Experiments 2-3: Interactions Between B, I and S

Experiment 2: B does not Influence Glucose Lowering Effects of I or S

C57BL/6 mice were fed a HFD or LFD for 4 weeks and received B, I and B (I+B), S and B (S+B) and the mix at 3.3 mg/kg of each compound (diluted in 0.9% NaCl/5% ethanol) orally 1 h before an ipGTT was performed (n=4-10/group). I+B, S+B and the mix significantly improved glucose tolerance.

Figure 2:
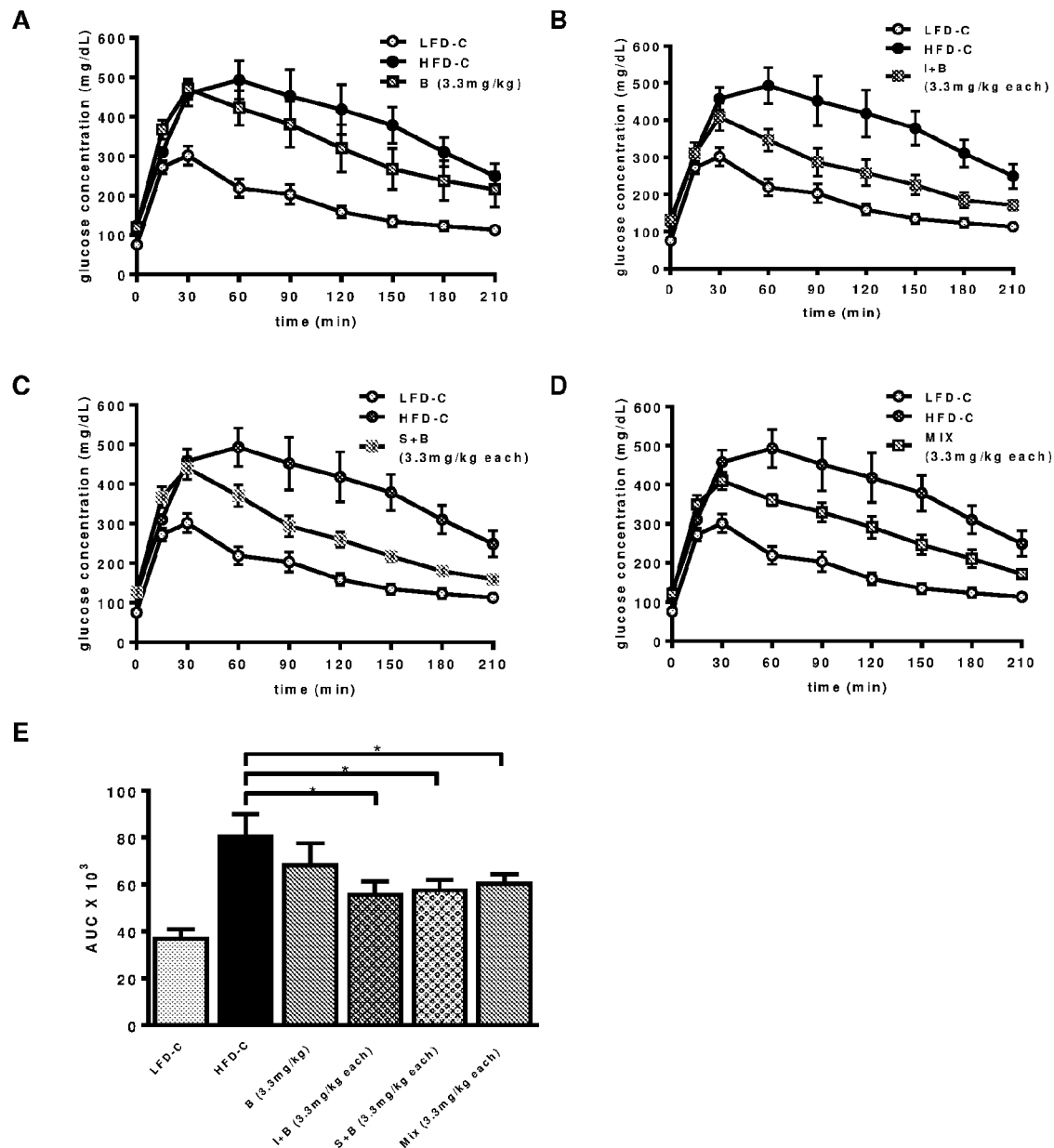
FIGS. 2A-D show graphs of ipGTT results on C57BL/6 mice fed (1) a high fat diet (HFD) for 4 weeks; (2) a low fat diet (LFD) for 4 weeks or (3) a high fat diet for 4 weeks and followed by treatment with butein (A), a 1:1 combination of butein and isoliquiritigenin (B), a 1:1 combination of butein and sulfuretin (C) and a 1:1:1 mixture of butein, sulfuretin and isoliquiritigenin (D).
FIG. 2E shows a bar graph comparing the area under the curve for the ipGTT results shown in FIGS. 2A-D.

Experiment 2 tests interactions of B with either I or S. As expected, 4 weeks of HFD feeding led to glucose intolerance in comparison with mice fed a LFD (p<0.0001). The compounds and formulations were given orally one hour before the ipGTT. B (3.3 mg/kg) alone showed no effect on glucose tolerance at either time point consistent with the findings in experiment 1. However, B in combination with I (3.3 mg/kg body weight each; p=0.0230) and B in combination with S (3.3 mg/kg body weight each; p=0.0142) improved glucose tolerance significantly. Additionally, mice treated with the mix of all three compounds (3.3 mg/kg body weight of each compound) showed improved glucose homeostasis (p=0.0216) compared with vehicle treated mice on HFD (FIG. 2D). Like in experiment 1, oral application of B alone did not improve glucose homeostasis. However, when administered together with I or S the glucose lowering potential of these compounds was not affected negatively by B, in the contrary, the data suggests that B may improve the action of I (cf. experiment 1).

Experiment 3: I+S Inhibit Each Other in the Absence of B

C57BL/6 mice were fed a HFD or LFD for 4 weeks and received I or S, I and S (I+S), or the mix at 3.3 mg/kg (diluted in 0.9% NaCl/5% ethanol) orally 1 h before an ipGTT was performed (n=5-7/group). I or S incline to improve glucose tolerance while this effect was abolished in the presence of both.

Having established that oral application of B on its own is not effective in improving glucose homeostasis but does not negatively affect the action of I and S, we next tested whether I and S interact with each other and thereby alter their effects on regulation of glucose homeostasis. Therefore, HFD-fed mice were treated either with I or S individually with I and S in combination or with the mix of I, S and B. After 4 weeks of feeding mice a HFD or LFD, the HFD-fed animals were glucose intolerant as expected (p=0.0005). Mice treated with I (FIG. 3A; 3.3 mg/kg; p=0.0308) or S (FIG. 3B; 3.3 mg/kg; p=0.0257) individually or with the mix (FIG. 3D; 3.3 mg/kg each; p=0.0561) showed improved glucose tolerance or a strong trend respectively, while surprisingly the effect was completely abolished when mice were treated with I in combination with S (3.3 mg/kg each).

Experiments 4-5: Dose Response of Mix and Extract

To determine the relative potencies of the compounds to improve glucose homeostasis, a dose response of the mix and the extract was performed. Mice were treated with five different concentrations ranging from 0.33 mg/kg up to 20 mg/kg and 50 mg/kg body weight, respectively.

Experiment 4: Dose Response for Mix (4 Weeks Diet)

C57BL/6 mice were fed a HFD or LFD for 4 weeks and received the mix at different concentrations (diluted in 0.9% NaCl/5% ethanol) orally 1 h before an ipGTT was performed (n=4-6/group).

Figure 4:
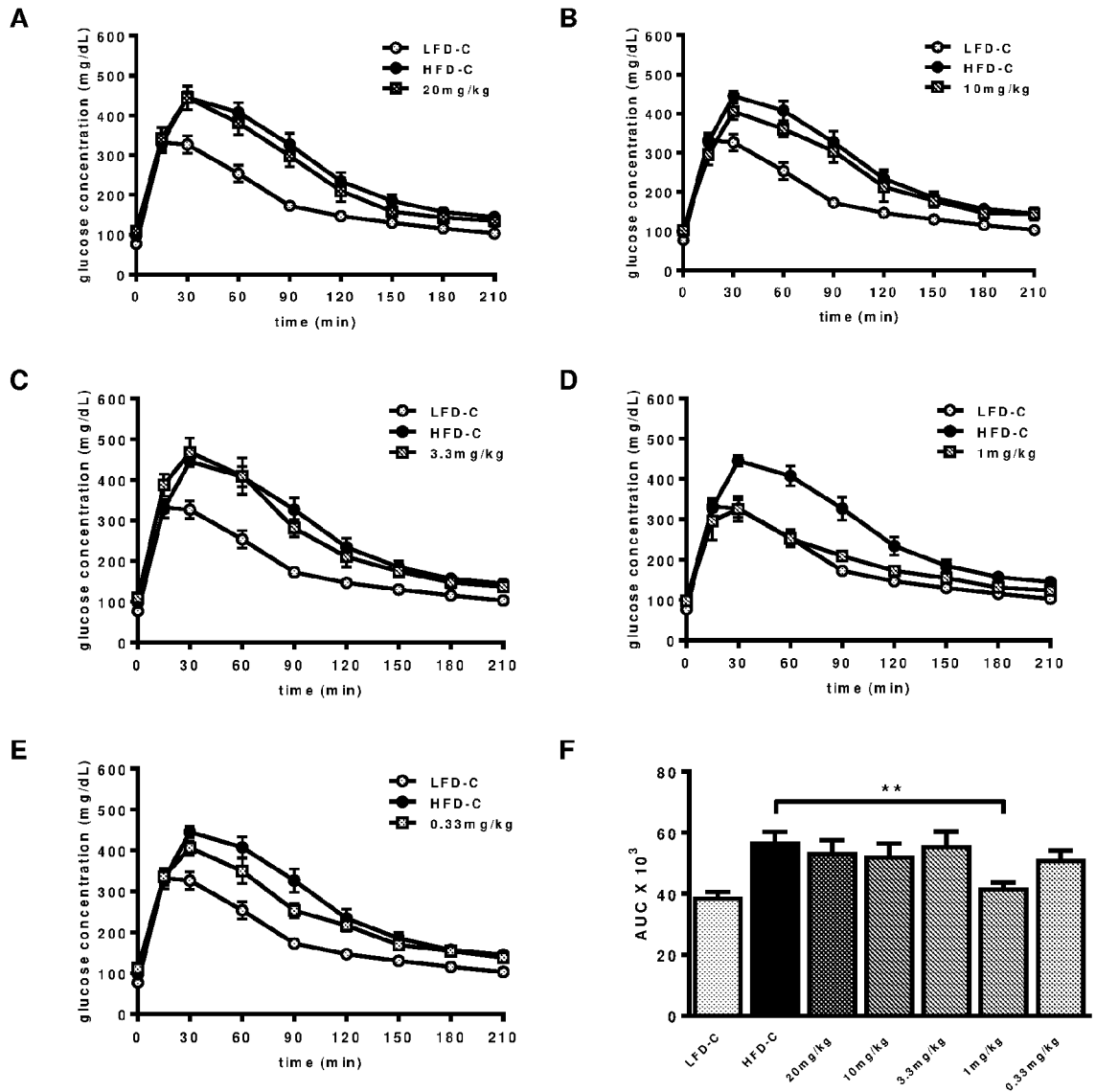
FIGS. 4A-E show graphs of ipGTT results on C57BL/6 mice fed (1) a high fat diet (HFD) for 4 weeks; (2) a low fat diet (LFD) for 4 weeks or (3) a high fat diet for 4 weeks and followed by treatment with a 1:1:1 mixture of butein, sulfuretin and isoliquiritigenin the mix at different concentrations (20 mg/kg (A), 10 mg/kg (B), 3.3 mg/kg (C), 1 mg/kg (D) or 0.33 mg/kg (E) body weight) by oral gavage one hour before an ipGTT.
FIG. 4F shows a bar graph comparing the area under the curve for the ipGTT results shown in FIGS. 4A-E.

Either LFD or HFD was fed for 4 weeks and mice were then treated with the mix at different concentrations (20, 10, 3.3, 1 or 0.33 mg/kg body weight) by oral gavage one hour before an ipGTT was performed (FIG. 4). As expected, after 4 weeks on HFD mice displayed a significantly impaired glucose tolerance compared with mice on LFD (p=0.0002). The mix showed a trend towards improving glucose tolerance at all concentrations. In particular, at 1 mg/kg body weight a striking reversal of DIO-induced glucose intolerance was observed (p=0.0060) with the AUC being no longer different to healthy mice on LFD (FIG. 4F). These data suggest that the mix is highly potent at reversing glucose intolerance when administered in an effective amount.

Experiment 5: Dose Response for Extract (4 Weeks Diet)

C57BL/6 mice were fed a HFD or LFD for 4 weeks and received the extract at different concentrations (diluted in 0.9% NaCl/5% ethanol) orally 1 h before an ipGTT was performed (n=6-7/group).

Figure 5:
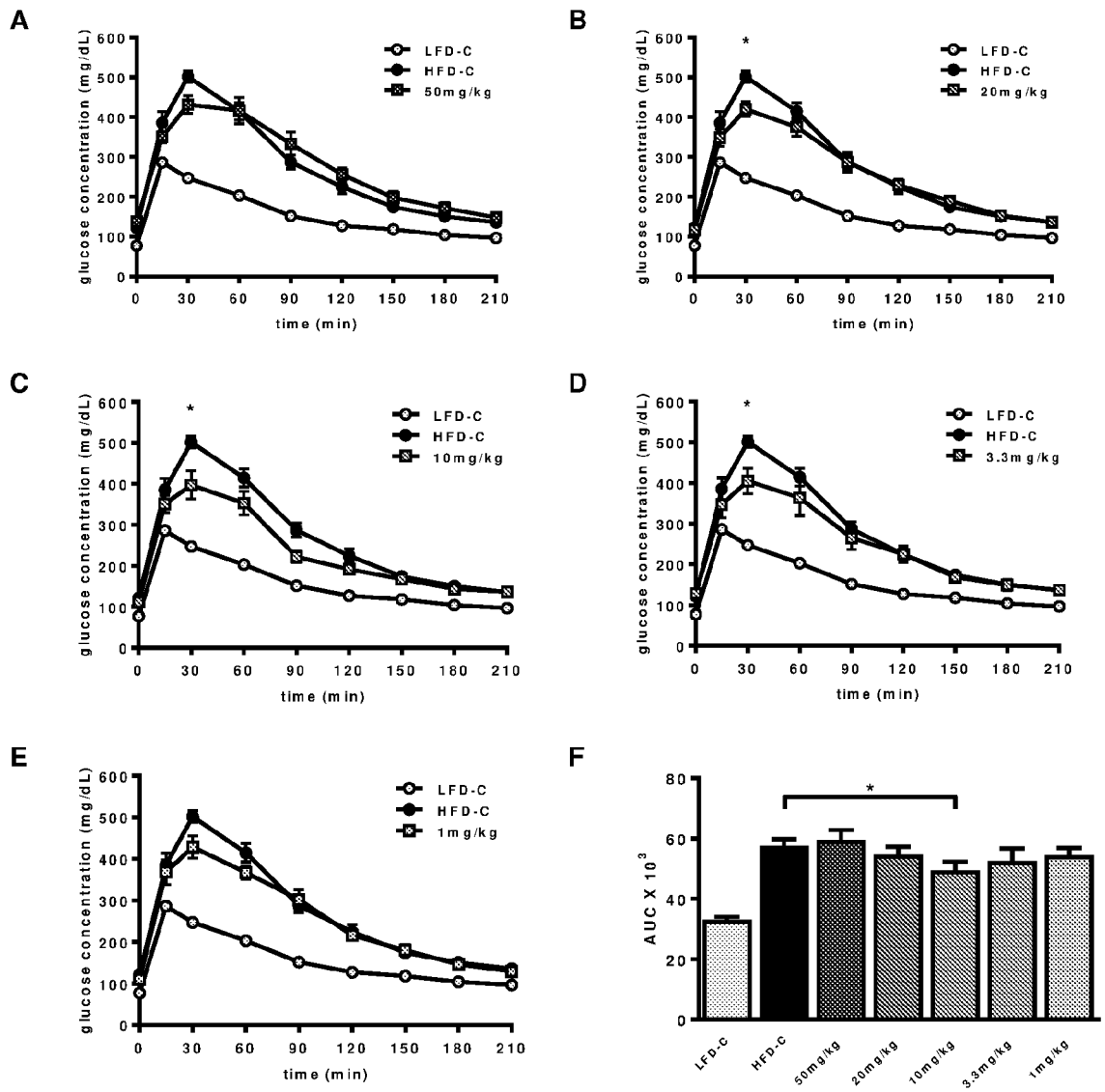
FIGS. 5A-E shows graphs of ipGTT results on C57BL/6 mice fed (1) a high fat diet (HFD) for 4 weeks; (2) a low fat diet (LFD) for 4 weeks or (3) a high fat diet for 4 weeks and followed by treatment with an extract of a *Dahlia* plant comprising butein, sulfuretin and isoliquiritigenin at different concentrations (50 mg/kg (A), 20 mg/kg (B), 10 mg/kg (C),3.3 mg/kg (D) or 1 mg/kg (E) body weight) by oral gavage one hour before an ipGTT.
FIG. 5F shows a bar graph comparing the area under the curve for the ipGTT results shown in FIGS. 5A-E.

For this part of the study the extract of *Dahlia* petals was administered to mice that were on HFD for 4 weeks. The concentration of the three main active compounds in the extract (1 mg) was about 0.076 mg each, thus 13 times lower compared to the mixture at the equivalent concentration (1 mg). Accordingly, in comparison to Experiment 4, a higher dose of 50 mg/kg body weight was selected as the highest dose due to the relative lower concentration of the individual compounds in the extract and due to the fact that the extract was more soluble in the vehicle (0.9% NaCl containing 5% ethanol). As expected, 4 weeks of HFD feeding impaired glucose tolerance in mice compared with mice on LFD (p<0.0001). The extract showed a trend towards an improvement in glucose tolerance in a hormetic manner with the middle dose of 10 mg/kg body weight, being the most effective and attaining significance (p=0.0482) compared with the HFD control mice (FIG. 5). Moreover, individual analysis at the different time points revealed that the extract decreased glucose levels significantly at time point 30 min at 20 mg/kg (p=0.0212), 10 mg/kg (p=0.0402) and 3.3 mg/kg (p=0.0375) compared to the HFD control group (FIG. 5).

The most effective dose of the extract is ten times higher (Experiment 5; 10 mg/kg) than of the mix (Experiment 4; 1 mg/kg). However, the total amount of the three compounds is similar in the extract (Experiment 5; 0.76 mg/kg) compared to the mix (Experiment 4; 1 mg/kg). Therefore, these experiments show that the concentration of B, S and I needed to elicit the maximum observed antidiabetic effect is similar for the mix and the extract, suggesting that the combination of B and S and/or I provides the majority of the observed efficacy.

Experiments 6-7: Interaction Mix and Metformin

The dose response experiments revealed that the mix can reverse glucose intolerance at 1 mg/kg body weight in mice fed a HFD for 4 weeks. To assess effects of the mix in combination with the widely prescribed diabetes drug metformin both at lower than their maximal effective dose, we first assessed the highest dose at which metformin was unable to improve glucose tolerance (Experiment 6). The combination of this subclinical dose of metformin is then tested in combination with the mix (Experiment 7).

Experiment 6: Dose Response for Metformin (4 Weeks Diet)

C57BL/6 mice were fed a HFD or LFD for 4 weeks and metformin was administered orally at different concentrations (diluted in PBS, pH7.7) twice daily for the last 7 days of the experiment (12 hourly). HFD-C and LFD-C mice received vehicle (PBS). An ipGTT was performed (n=5-7/group) and metformin significantly improved glucose tolerance when given at 300 mg/kg/d.

Figure 6:
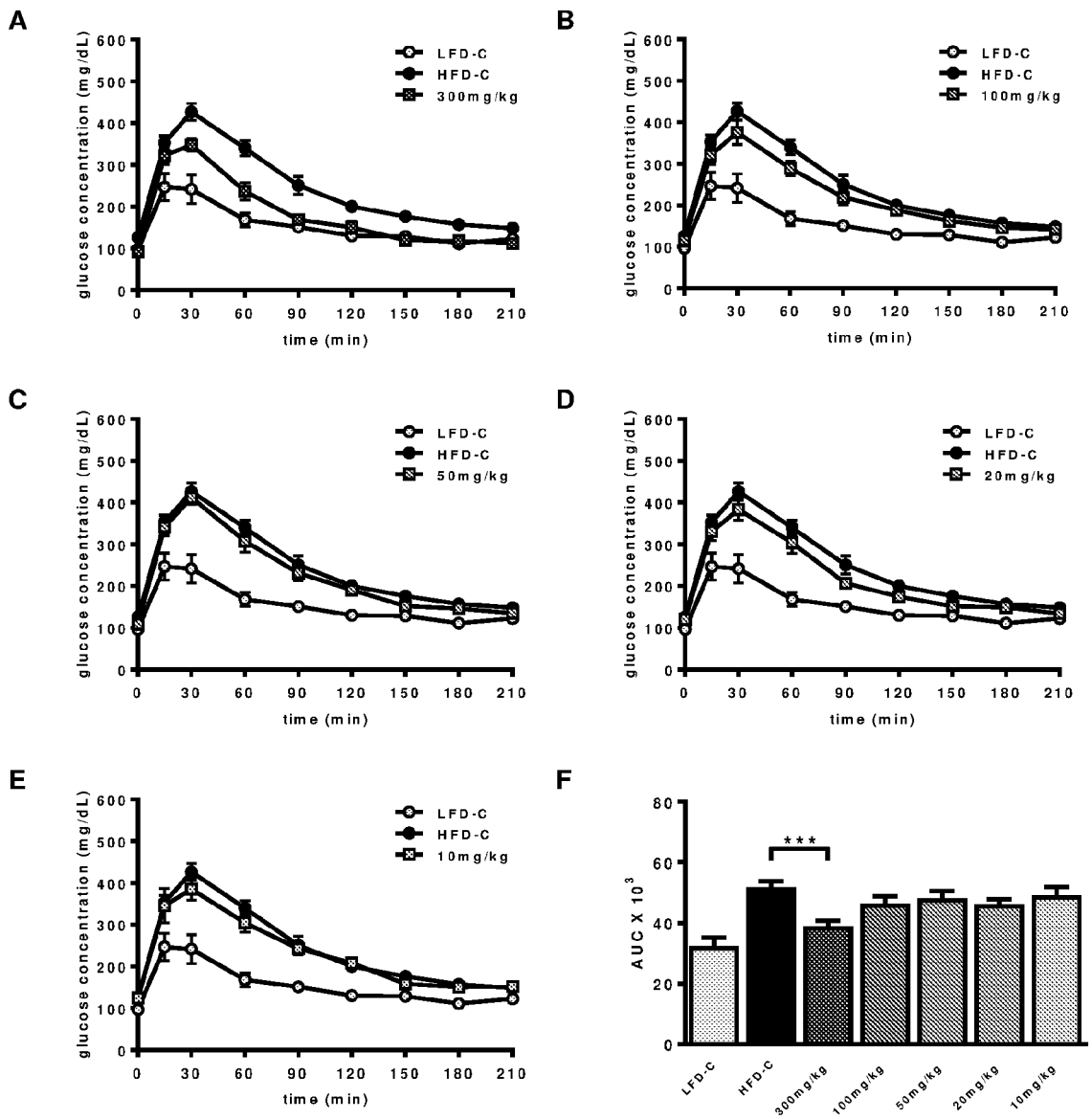
FIGS. 6A-E show graphs of ipGTT results on C57BL/6 mice fed (1) a high fat diet (HFD) for 4 weeks; (2) a low fat diet (LFD) for 4 weeks or (3) a high fat diet for 4 weeks with treatment with metformin (diluted in phosphate buffered saline (PBS), pH7.7) administered orally for the last 7 days at 300 mg/kg/d (A), 100 mg/kg/d (B), 50 mg/kg/d (C), 20 mg/kg/d (D) and 10 mg/kg/d (E), twice daily, 12 hourly.
FIG. 6F shows a bar graph (F) comparing the area under the curve for the ipGTT results shown in FIGS. 6A-E.
Figure 7:
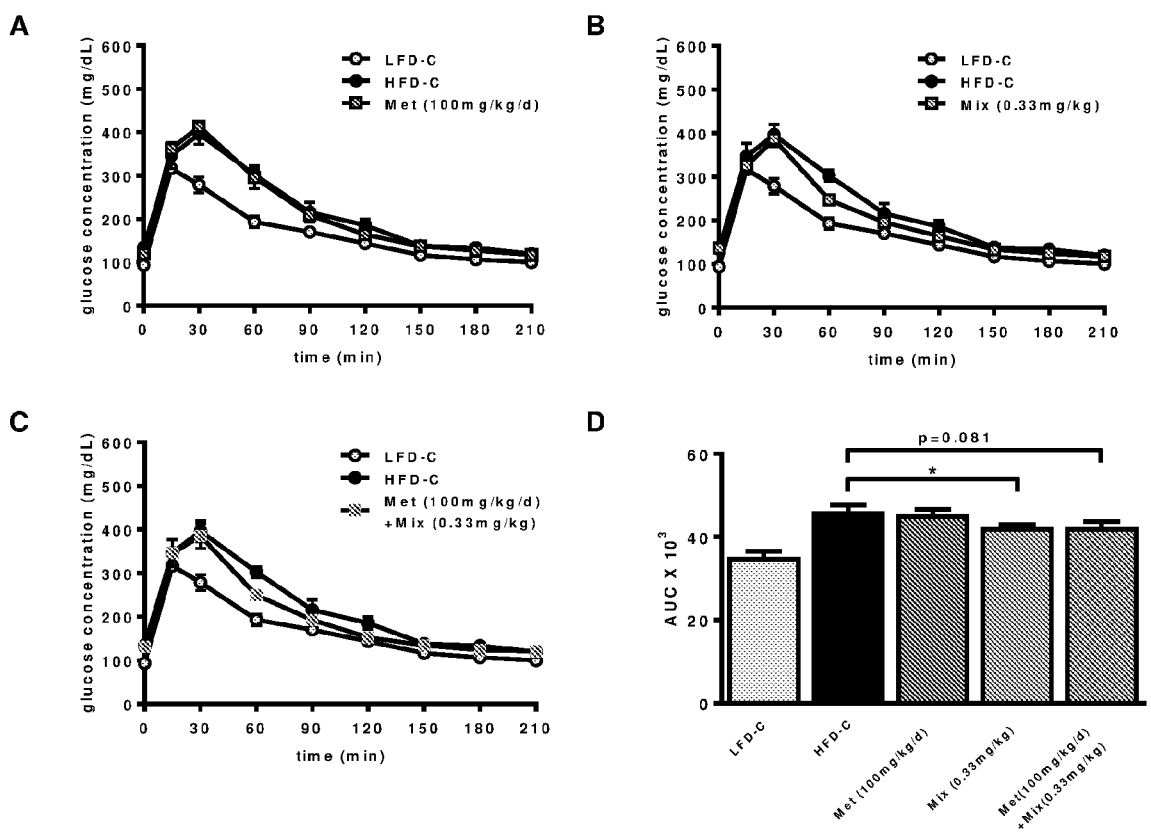
FIGS. 7A-C show graphs of ipGTT test results on C57BL/6 mice fed (1) a high fat diet (HFD) for 4 weeks; (2) a low fat diet (LFD) for 4 weeks; (3) a high fat diet for 4 weeks with treatment for the last 7 days with metformin (100 mg/kg/d orally twice daily, 12 hourly; A); (4) a high fat diet for 4 weeks and administration 1 hour prior to ipGTT of a 1:1:1 mixture of butein, sulfuretin and isoliquiritigenin (mix; 0.33 mg/kg; B); or (5) a high fat diet for 4 weeks with treatment with metformin administered for the last 7 days (100 mg/kg/d orally twice daily, 12 hourly) and administration 1 hour prior to ipGTT of the mix (0.33 mg/kg; C).
FIG. 7D shows a bar graph comparing the area under the curve for the ipGTT results shown in FIGS. 7A-C.

Mice were fed a HFD for 4 weeks and received metformin twice daily by oral gavage for the last week. As expected, after 4 weeks being fed a HFD mice showed a significantly impaired glucose tolerance compared to the LFD mice (p=0.0001). As expected, twice daily injections of metformin improved glucose tolerance compared with the HFD control group, however, this was dose dependent with only the very high concentration of 300 mg/kg being effective (FIG. 6; p=0.004). The highest dose at which metformin did not improve glucose tolerance was determined to be 100 mg/kg body weight.

Experiment 7: Metformin in Combination with Mix (4 Weeks Diet)

C57BL/6 mice were fed a HFD or LFD for 4 weeks and metformin was orally administered at 100 mg/kg (diluted in PBS, pH7.7) daily for the last 7 days (12 hourly). 1 h before the ipGTT mice received the mix or saline, respectively (n=6-7/group).

In Experiment 6 the highest non-effective dose of metformin was determined to be 100 mg/kg body weight, which led co-administration of metformin at this concentration with the highest non-effective dose of the mix (0.33 mg/kg body weight, Experiment 4) to determine possible synergistic effects. Mice were fed either a LFD or HFD for 4 weeks and metformin was given daily by oral gavage for the last 7 days of the experiment (as for experiment 6). One hour before the ipGTT, mice received the mix orally. As expected glucose tolerance was significantly impaired in HFD control animals compared with the LFD mice (FIG. 6; p=0.0002). As in experiment 6, there were no differences between the metformin treated mice and the HFD control mice confirming that the dose on its own was ineffective (FIG. 6A). In this experiment, the mix alone was able to improve glucose tolerance slightly (FIG. 6B; p=0.0308) and there was a strong trend towards a significantly decreased AUC in the group which received metformin and the mix (FIG. 6D, p=0.081).

Experiments 8 and 9: Pramlintide in Combination with Mix

The same procedure used with metformin in Experiments 6 and 7 was also used with pramlintide. First, the highest non-effective dose of pramlintide in HFD-fed mice was determined, followed by a co-administration of the highest non-effective dose of the mix and the lowest non-effective dose of pramlintide.

Experiment 8: Dose Response for Pramlintide (4 Weeks Diet)

C57BL/6 mice were fed a HFD or LFD for 4 weeks and pramlintide was given s.c. at different concentrations (diluted in PBS, pH7.7) daily for the last 5 days (12 hourly). An ipGTT was performed (n=5-7/group) and pramlintide significantly improved glucose tolerance when given at 1 mg/kg/d.

Figure 8:
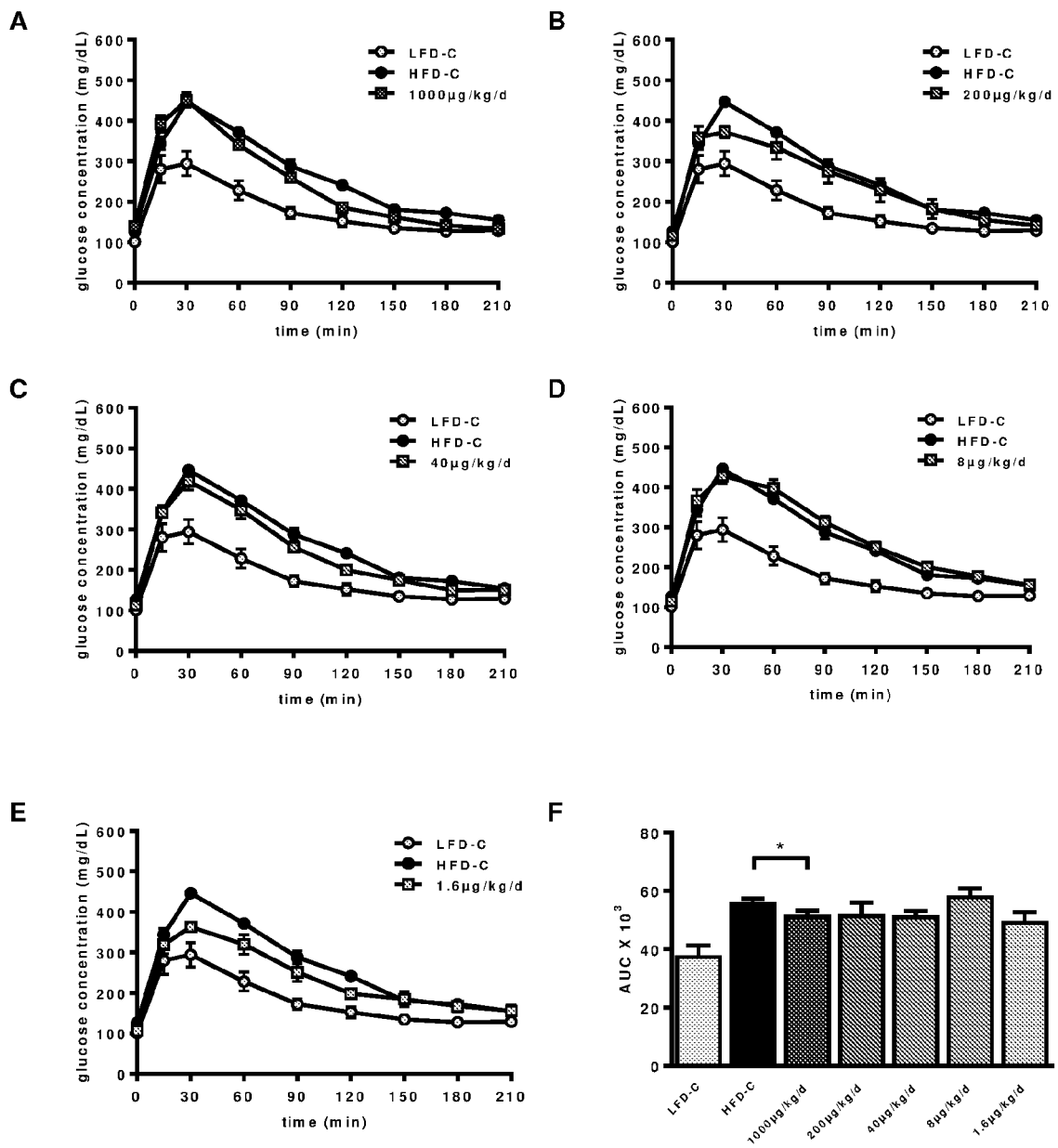
FIGS. 8A-E show graphs of ipGTT results on C57BL/6 mice fed (1) a high fat diet (HFD) for 4 weeks; (2) a low fat diet (LFD) for 4 weeks or (3) a high fat diet for 4 weeks with treatment with pramlintide (subcutaneous injection for last 5 days of treatment, twice daily, 12 hourly) at 1000 μg/kg/d (A), 200 μg/kg/d (B), 40 μg/kg/d (C), 8 μg/kg/d (D) and 1.6 μg/kg/d (E).
FIG. 8F shows a bar graph comparing the area under the curve for the ipGTT results shown in FIGS. 8A-E.

Mice were fed a HFD for 4 weeks and received pramlintide subcutaneously (s.c.) twice daily for 5 days. As expected mice on HFD had a significantly impaired glucose tolerance compared with mice on LFD (p=0.0002). At the highest tested dose of 1000 µg/kg/d body weight pramlintide improved glucose tolerance (p=0.0497) significantly compared to vehicle injected mice on HFD, whereas the other concentrations had no significant effect on glucose homeostasis (FIG. 8).

Experiment 9: Pramlintide in Combination with Mix (4 Weeks Diet)

C57BL/6 mice were fed a HFD or LFD for 4 weeks and pramlintide was administered s.c. at 200 µg/kg/d (diluted in PBS, pH7.7) for the last 5 days. 1 h before the ipGTT mice received the mix or saline, respectively (n=12-15/group).

Figure 9:
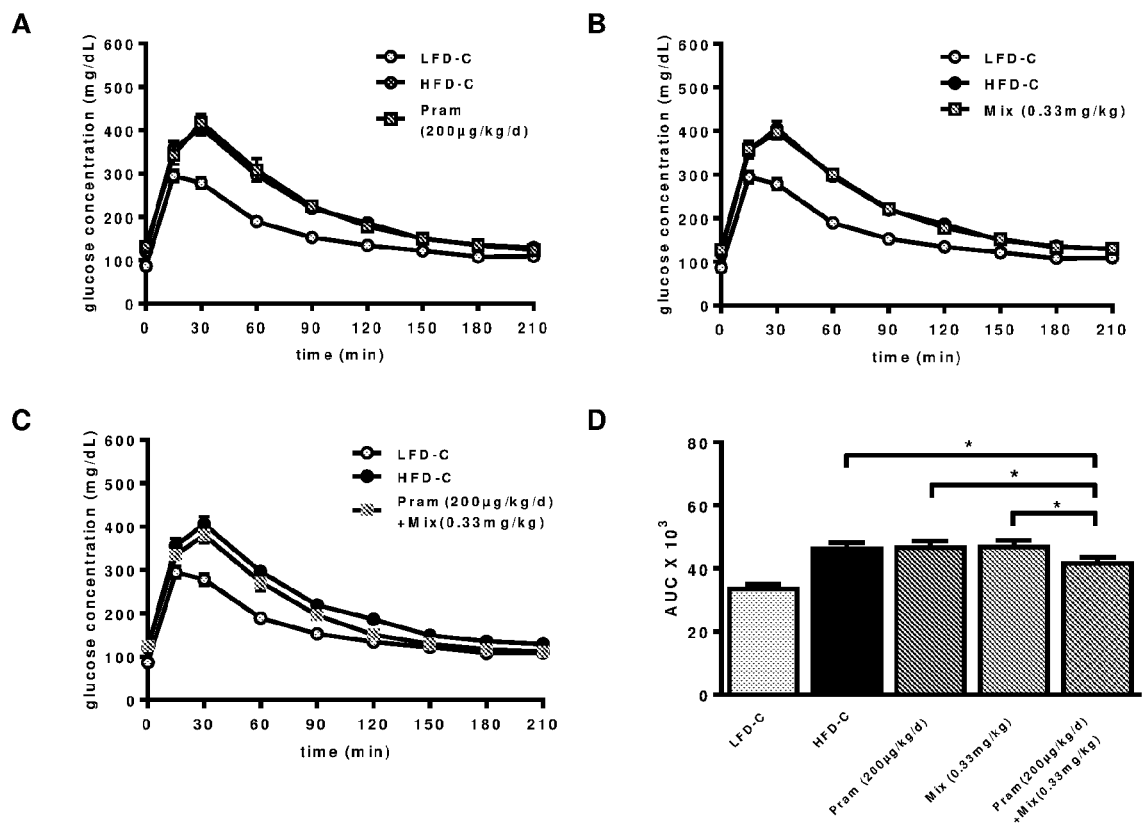
FIGS. 9A-C show graphs of ipGTT test results on C57BL/6 mice fed (1) a high fat diet (HFD) for 4 weeks; (2) a low fat diet (LFD) for 4 weeks; (3) a high fat diet for 4 weeks with treatment for the last 5 days with pramlintide (200 μg/kg/d subcutaneous; twice daily; 12 hourly; A); (4) a high fat diet for 4 weeks and administration 1 hour prior to ipGTT of a 1:1:1 mixture of butein, sulfuretin and isoliquiritigenin (mix; 0.33 mg/kg; B); or (5) a high fat diet for 4 weeks with treatment with pramlintide administered subcutaneously for the last 5 days (200 μg/kg/d; twice daily; 12 hourly) and oral administration 1 hour prior to ipGTT of the mix (0.33 mg/kg; C).
FIG. 9D shows a bar graph (D) comparing the area under the curve for the ipGTT results shown in FIGS. 9A-C.

Mice received either a LFD or a HFD for 4 weeks and were treated with the highest non-effective dose of pramlintide (200 µg/kg/d body weight) or vehicle (PBS) for the last 5 days. Two groups of mice received the mix at the highest non-effective dose (0.33 mg/kg body weight) in addition to pramlintide or saline by oral gavage one hour before the ipGTT. As expected glucose tolerance was impaired significantly in the HFD control mice compared to the LFD mice (p<0.0001). As anticipated neither pramlintide alone at 200 µg/kg/d body weight (FIG. 9A) nor the mix at 0.33 mg/kg body weight (FIG. 9B) was able to improve glucose tolerance individually; however, given in combination glucose tolerance was improved significantly compared with the HFD mice which received vehicle (FIGS. 9C and 9D; p=0.0178). These data support that pramlintide and the mix reveal a synergistic effect on improving glucose tolerance.

Experiment 10: Effects of Mix and Extract on Insulin Signalling in the Hypothalamus To investigate the molecular mechanisms and to identify the molecular targets of the mix and the extract, mice were fed either a HFD or LFD for 4 weeks followed by treatment with the mix (3.3 mg/kg body weight each) or the extract (10 mg/kg) acutely by oral gavage. One hour after oral gavage, mice underwent transcardial perfusion, received insulin i.p. (1 mg/kg body weight) 15 minutes before perfusion and brains were prepared for molecular analysis. The target protein of the insulin signalling pathway, pAKT, was visualized by immunohistochemistry and quantified by counting pAKT immunoreactive cells.

Figure 10:
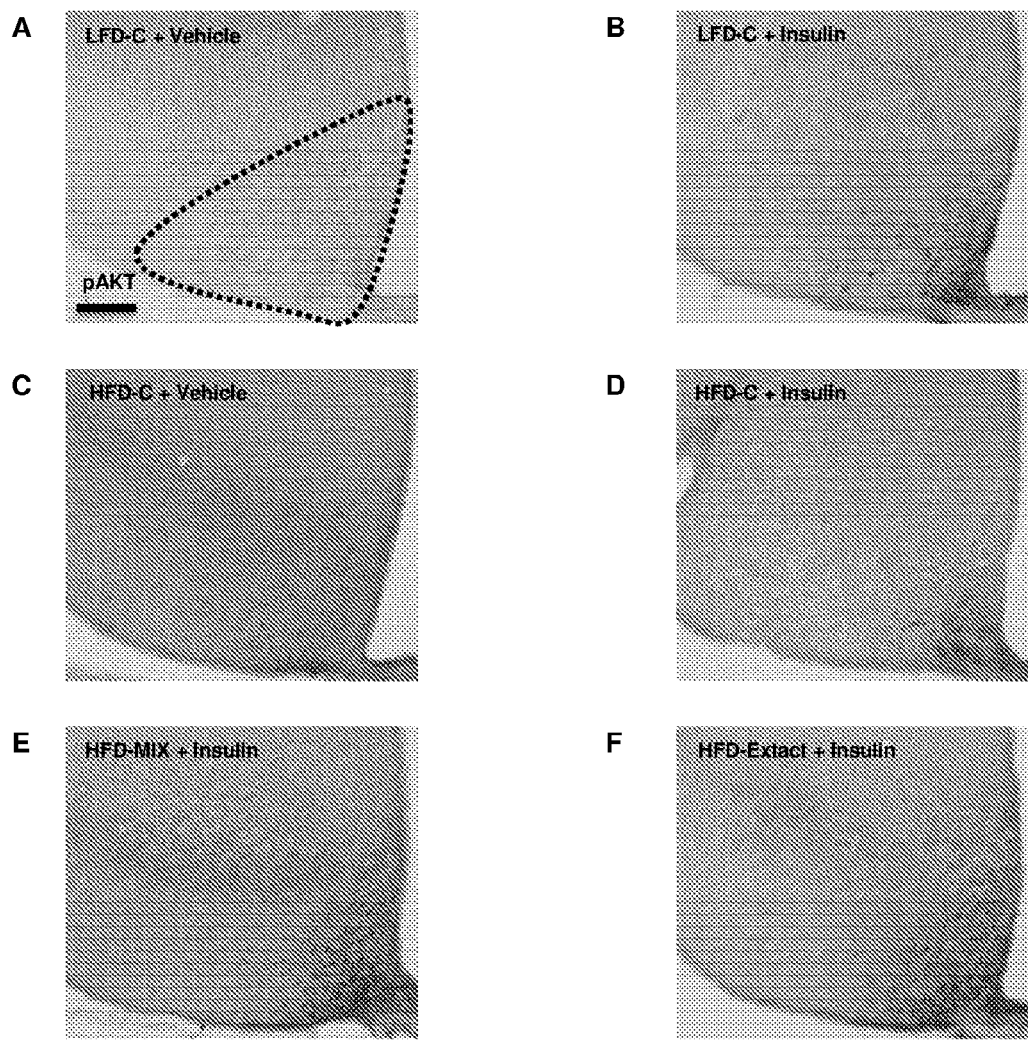
FIGS. 10A-F show images of immunohistochemically stained brain sections of C57BL/6 mice fed a HFD for 4 weeks and administered orally with the active ingredients (10 mg/kg) or vehicle (5% EtOH in saline—vehicle only, or vehicle and insulin) 1 h before transcardial perfusion.
Figure 11:
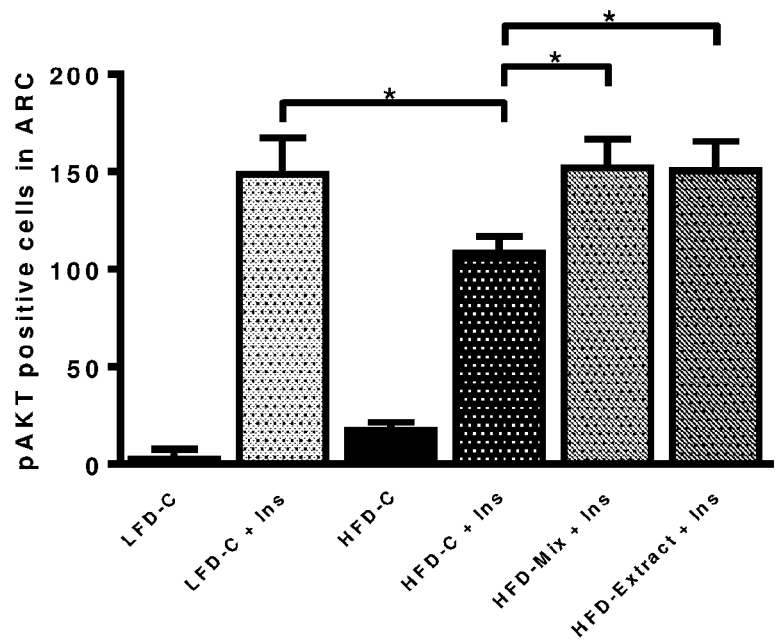
FIG. 11 shows a bar graph of the number of pAKT immunoreactive cells within the ARC (framed area) for the brain slice images of FIG. 10.

Fifteen minutes before transcardial perfusion, either insulin (1 mg/kg) or vehicle was injected, to activate the insulin signalling pathway. Insulin administration markedly increased pAKT positive cells in the arcuate nucleus of the hypothalamus of both LFD ($p<0.0001$) and HFD ($p<0.0001$) fed mice compared with the vehicle-injected group, respectively. While the basal number of pAKT positive cells was higher in mice fed HFD diet compared with LFD, insulin-increased the number of pAKT positive cells to a greater extent in LFD mice compared with HFD ($p=0.0479$) mice. This suggests that mice fed HFD for 4 weeks had reduced insulin sensitivity in the arcuate nucleus. The mix ($p=0.0257$) and the extract ($p=0.0419$) were both able to reverse this reduced insulin sensitivity so that numbers of pAKT positive cells within the arcuate nucleus were comparable to the healthy LFD control mice (FIGS. 10 and 11).

Experiment 11: Insulin Tolerance Test (ITT)

This experiment was conducted to determine the potential potency of the extract to improve insulin sensitivity an ITT was performed. Mice were acutely treated with the extract (10 mg/kg body weight) and then received an insulin injection (1 mg/kg).

Figure 12:
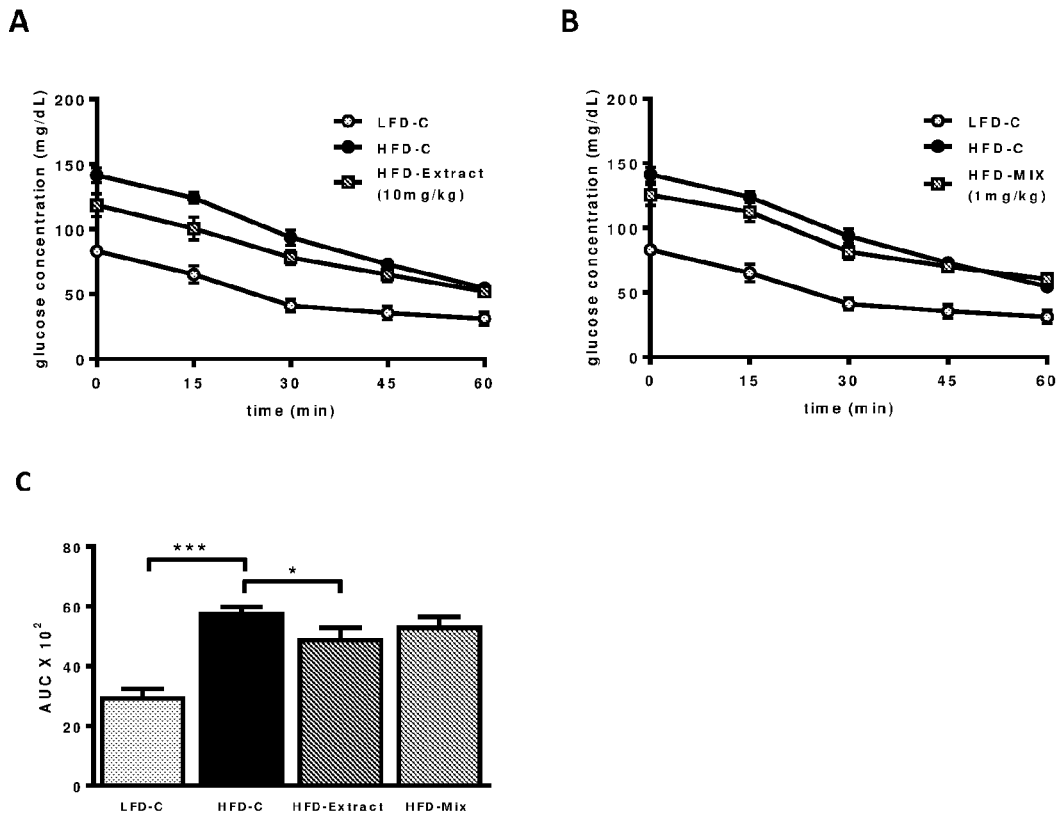
FIGS. 12*a-c* show (a,b) graphs of glucose concentration versus time from the insulin tolerance test described in Experiment 11 of Example 1 and (c) shows a graph of the Area Under the Curve (AUC) of the glucose concentrations shown in FIGS. 12*a* and 12*b*.

Mice received either a LFD or a HFD for 4 weeks and HFD-fed mice were then treated with the extract (10 mg/kg), mix (1 mg/kg body weight) or vehicle (0.9% NaCl) acutely by oral gavage one hour before the ITT was performed. After 4 weeks of HFD insulin sensitivity was significantly impaired compared with LFD ($p<0.001$). While the mix (FIG. 12b) had no effect on insulin sensitivity, the extract (FIG. 12a) improved insulin sensitivity significantly ($p=0.0416$; FIG. 12c).

Experiments 12-14: Chronic Administration of the Extract—GTT, Immunohistochemical Analysis of Brain Inflammation (GFAP and pIκBα) and Oil-Red-O Staining (ORO) of Liver Tissue These experiments were conducted to test for long term effects of the extract we fed mice either a HFD or LFD for 4 weeks (GTT) or 5 weeks (immunohistochemistry and liver histopathology) and simultaneously administered the extract (10 mg/kg/d) once daily by oral gavage. After 4 weeks we performed a GTT, after 5 weeks mice underwent transcardial perfusion (4% PFA) and brains were prepared for molecular analysis. Immunohistochemical analysis was carried out on brain slices for the inflammatory markers GFAP (astrocytes) and pIκBα (NFκB signalling pathway). Furthermore, liver tissue was excised before perfusion to analyse for liver pathology.

Experiment 12: Chronic Administration of the Extract—GTT (4 Weeks Diet)

Figure 13:
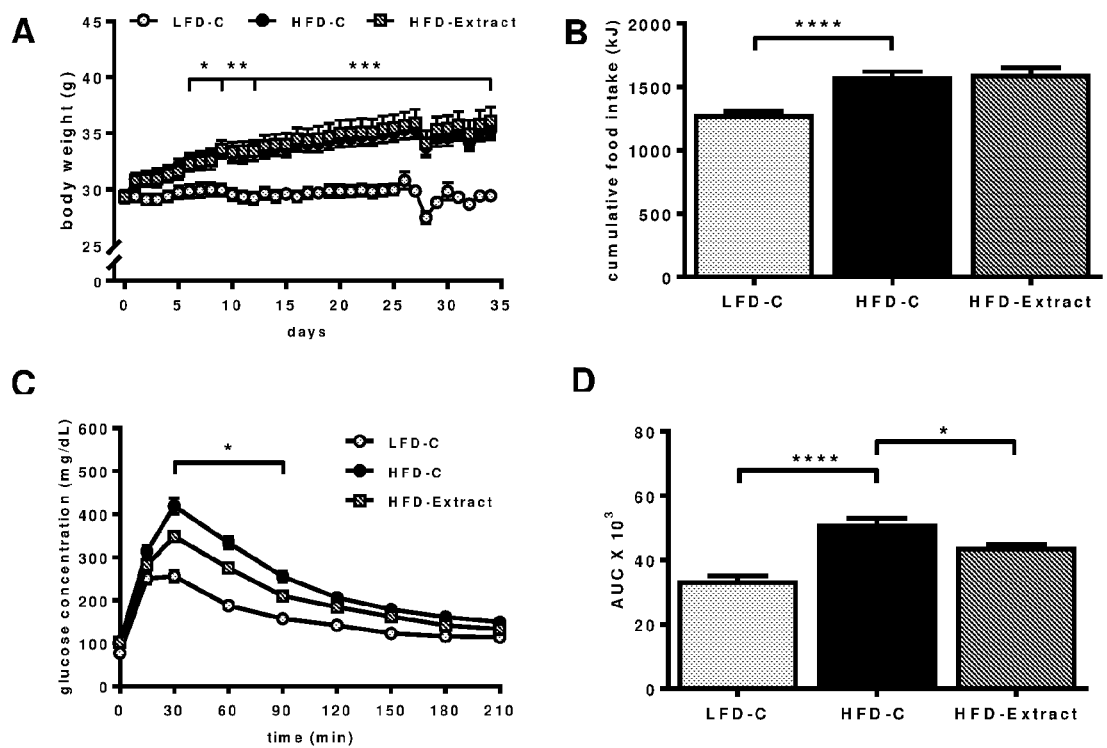
FIG. 13 shows (A) a graph of body weight over time for the mice subjects of Experiment 12 of Example 1; (B) AUC for the body weight data shown in FIG. 13A; (C) a graph of plasma glucose concentration over time obtained from Experiment 12 of Example 1; and (D) AUC for the body weight data shown in FIG. 13C.

Mice were fed either a LFD or a HFD for 4 weeks and received the extract (10 mg/kg/d body weight) once daily by oral gavage from day 1 on. After 4 weeks, body weight gain was significantly increased in mice fed a HFD ($p<0.001$) but unaltered between the HFD-C and HFD-extract group. Similar to body weight gain, cumulative food intake was significantly increased in the HFD groups ($p<0.0001$) but was identical between the HFD-C and HFD-Extract animals. Furthermore, HFD fed animals displayed significantly impaired glucose tolerance compared to LFD fed animals ($p<0.0001$). Despite no changes in body weight gain and food intake, chronic treatment with the extract for 4 weeks improved glucose tolerance significantly, compared to the HFD-C animals ($p=0.0166$, One-way-ANOVA; FIG. 13).

Experiment 13: Chronic Administration of the Extract—GFAP Stain (5 Weeks Diet)

Figure 14:
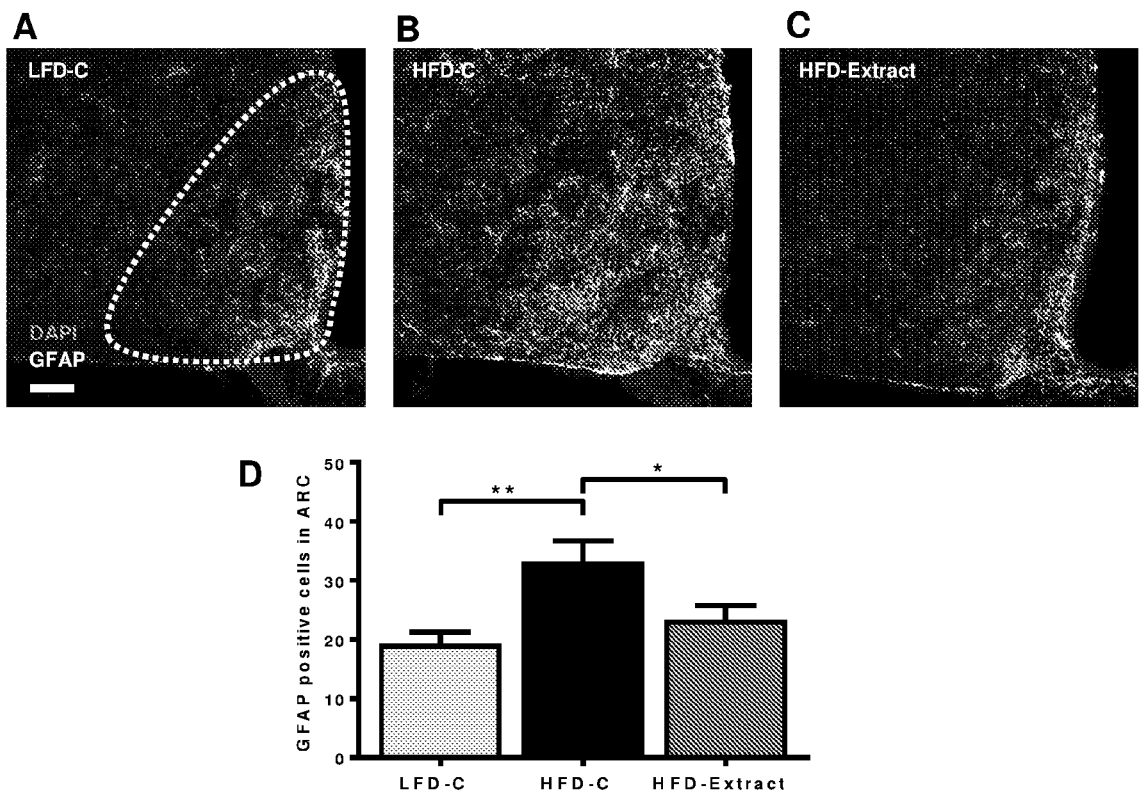
FIGS. 14A-D show (A-C) images of glial fibrillary acidic protein (GFAP) immunoreactive cells obtained from mice fed (A) LFD, (B) HFD or (C) HFD and treated with the extract; and (D) a chart of cell counts within the ARC (framed area) from the images from Experiment 13 of Example 1.

Mice received either a LFD or a HFD for 5 weeks and were simultaneously treated with the extract (10 mg/kg/d body weight) once daily by oral gavage. After 5 weeks, mice underwent transcardial perfusion (4% PFA) and brains were prepared for molecular analysis. Mouse brain coronal sections (30 μm) were stained for GFAP and immunoreactive cells within the arcuate nucleus of the hypothalamus (ARC) were counted by two investigators who were blinded to the treatment. Immunohistochemical analysis of mouse brains revealed a significant increase in the number of astrocytes the arcuate nucleus of the hypothalamus caused by the HFD ($p=0.0045$). In contrast, administration of the extract partially reversed this effect and mice treated with the extract showed a significant reduction in the number of astrocytes in compared to the HFD-C mice ($p=0.0479$; FIG. 14).

Experiment 14: Chronic Administration of the Extract—Liver Weight, H&E and ORO Staining This experiment evaluates the liver fat content and to unravel possible morphological changes in fat tissue, we performed an ORO staining as well as an H&E staining of liver tissue. Mice received either a LFD or a HFD for 5 weeks and were simultaneously treated with the extract (10 mg/kg/d body weight) once daily by oral gavage. After 5 weeks, liver tissue was excised just before transcardial perfusion and snap frozen in liquid nitrogen. Liver was cut into 8 μm sections, H&E and ORO staining was performed to analyse liver morphology. Furthermore, total liver weight was determined by dissecting the liver.

Figure 15:
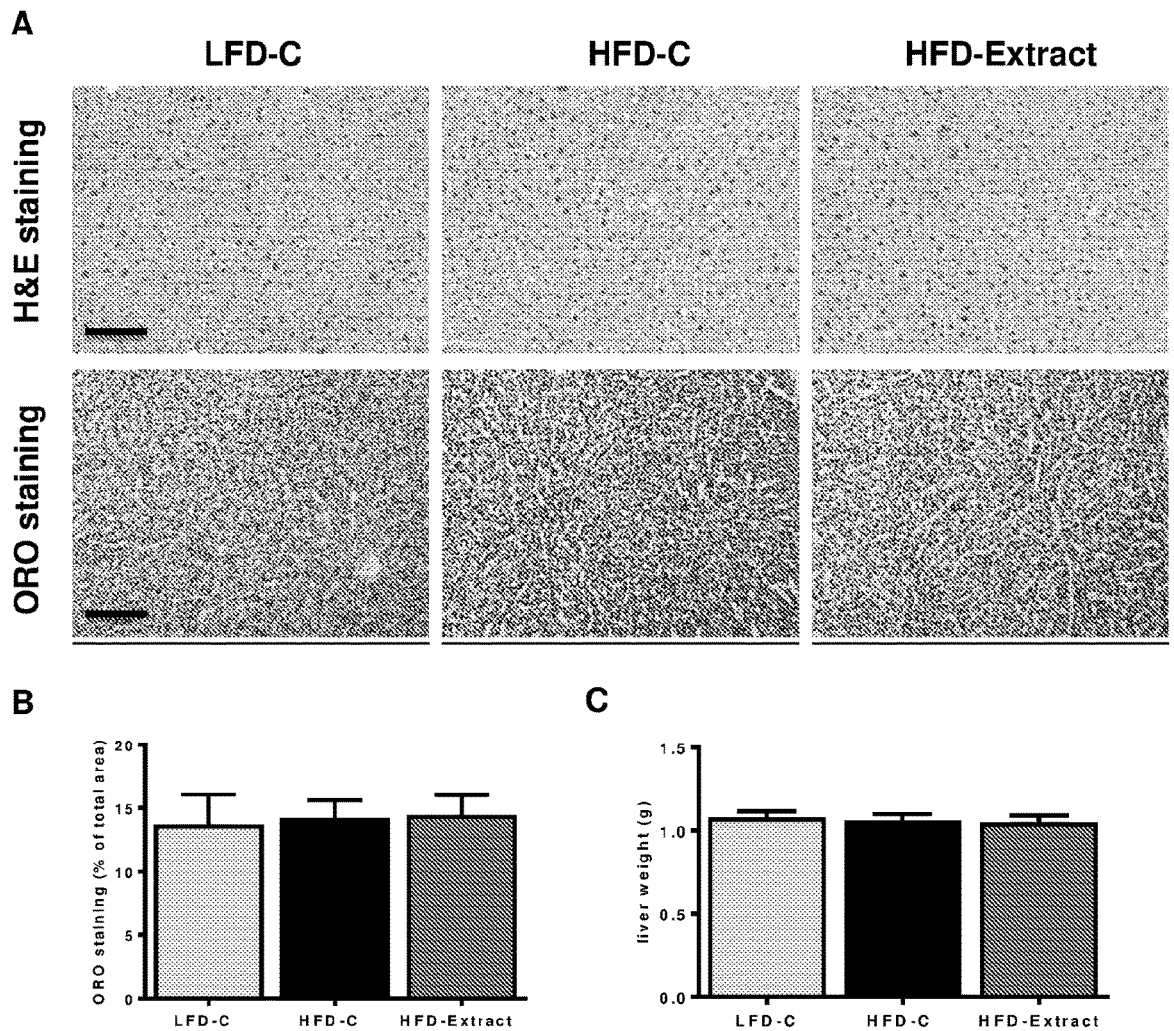
FIG. 15 shows (A) images of H&E or ORO stained cells prepared according to Experiment 14 of Example 1; (B) a graph of the proportion of ORO stained cells for each subject group from the data shown in FIG. 15A; and (C) liver weight of mice subjects obtained according to Experiment 14 of Example 1.

No differences among the groups were detected neither in liver H&E staining, liver ORO staining nor in total liver weight (FIG. 15).

Example 2: Stability of Extracts and of Pure Anthochlors In Vitro

Experiments were carried out on dissolving/dispersing *Dahlia* 'Ruskin Diane' extract into aqueous buffer. RPLC analysis showed a major change in composition over time.

To confirm the cause of instability of the buffered extract, the stability of butein was assessed in aqueous buffer at pH7 (butein was stable at pH4). There was a linear (zero order kinetics) conversion of butein to sulfuretin over time when either ethanol (EtOH) or dimethylsulfoxide (DMSO) solutions of butein were diluted into the aqueous buffer at room temperature (FIG. 16). By contrast, butein was stable when diluted into EtOH and stored under ambient conditions (FIG. 16). Butein has limited solubility in pH7 buffer solution and therefore some EtOH was required for solubility purposes.

The conversion of butein to sulfuretin is an oxidative cyclisation. Attempts to exclude oxygen slowed the reaction, but excluding light and adding a radical inhibitor had no effects on reaction rate.

A *Dahlia* extract showed the same conversion of butein to sulfuretin, but isoliquiritigenin decreased in concentration much more slowly and a corresponding aurone RPLC peak for isoliquiritigenin was not observed.

Example 3: Serum Insulin Concentration in Mice Fed a High-Fat Diet or a Low-Fat Diet Mice were fed either a high-fat diet containing 60% fat (HFD; cat. No. D12492; Research Diets) or a low-fat diet containing 10% fat (LFD; cat. no. D12450B; Research Diets) for 4 weeks. The insulin level in each test group was determined by ELISA (n=33/group). The mean serum insulin concentration for mice on HFD was about 0.75 ng/ml ($p=/<0.001$) which was significantly higher than the mean serum insulin concentration for mice on LFD (about 0.48 ng/ml) (see FIG. 17). These results suggest that the mice on HFD were hyperinsulinemic.

Figure 20:
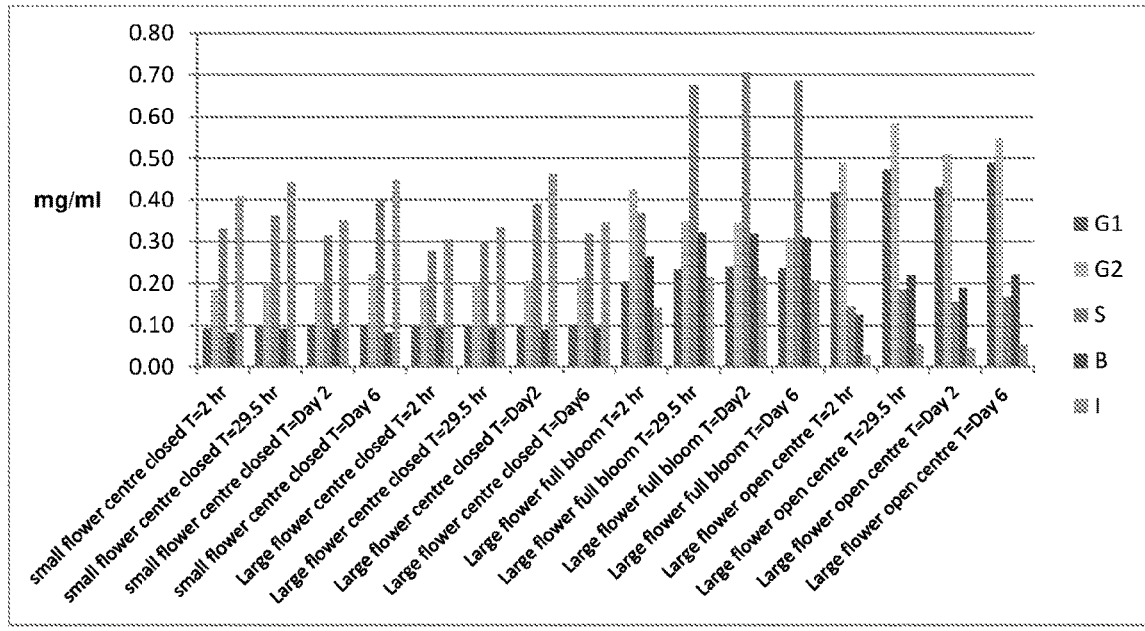
FIG. 20 shows a graph of the amount of the main compounds isolated from the petals of fresh *Dahlia* flowers of different maturation stages (G1=Butein glycoside, G2=Isoliquiritigenin glycoside, S=Sulfuretin, B=Butein, I=Isoliquiritigenin).
Figure 21:
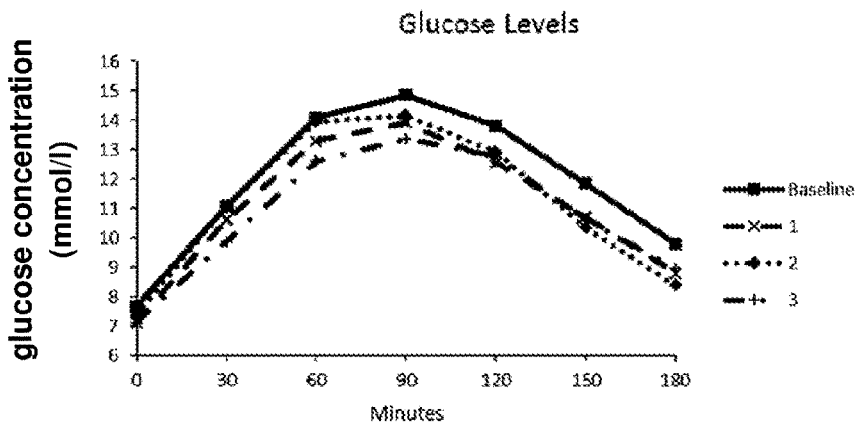
FIG. 21 shows a graph of the averaged glucose concentration results of Example 5 during an oral glucose tolerance test.

Example 4: Analysis of Compounds Contained in Extracts of *Dahlia* Petals Harvested at Different Maturation Stages of the Plant The petals (floret) were removed from the bracts and receptacle of 5 fresh dahlia flowers of different maturation stages. These varied from small bloom with the centre intact (closed), through to fully mature large flowers with the centre fully open. The fresh petals were extracted in ethanol (96%), using the ratio 1 part petal to 3 parts ethanol) and sampled at T=2 hours and T=2 days. The extracts were analysed by RPLC and the results are shown in FIG. 20.

Example 5: Clinical Trial Assessing the Efficacy of Combinations of BTN, SLF and ILQ in the Treatment of Pre-Diabetes and Type-2 Diabetes This clinical trial provides initial evidence of the safety and effectiveness of compositions of the invention in improving glucose metabolism in humans.

Research Design and Methods:

Design: This trial was designed as a sequential, crossover double blinded study of the effect of different doses of a composition of the invention on glucose metabolism following an oral glucose load.

Participants: Fourteen (14) male participants, with pre-diabetes or diabetes, were recruited in this study. Of these participants, 10 have completed treatments with all dosage levels tested and the results for these participants are outlined in Tables 6-9, below. All participants recorded a HbA1c level from 41 mmol/mol to 60 mmol/mol. A participant was considered to have prediabetes if their haemoglobin A1c (HbA1c) level was 41-49 mmol/mol, and a participant was considered to have diabetes if their HbA1c level was 50-60 mmol/mol.

Exclusion(s):
a. Any prior or current history of type 2 diabetes requiring oral medication other than metformin or requiring insulin therapy;
b. Any prior or current history of type 1 diabetes;
c. Taking any other treatment for prediabetes/diabetes other than lifestyle management or metformin only treatment;
d. Previous bariatric surgery;
e. Liver disease or a ratio of aspartate transaminase to alanine transaminase (AST/ALT) at least 3 times the upper limit of normal (ULN);
f. Renal disease or estimated glomerular filtration rate (eGFR) of less than 60; and/or
g. Known cardiac disease.

Preparation of compositions: *Dahlia* plant material was extracted according to liquid extraction methodology described herein. Residual extractant was removed to provide the extract as a powdered solid. Three (3) unit dose formulations were prepared to provide capsules of 3 different concentrations of the active combination: (i) 5 mg; (ii) 20 mg; and (iii) 50 mg. To prepare each unit dose formulation, an appropriate amount of the powdered solid extract was combined with an appropriate amount of microcrystalline cellulose to make up to a total mass, which was then filled into hydroxypropyl methyl cellulose capsule shells. The dose specified for each capsule relates to the mass of powdered solid extract contained in the capsule. For example, to prepare 50 mg capsules, a mixture of 50 wt % powdered solid extract and 50 wt % MCC was prepared, followed by freeze-drying and filling into HPMC capsule shells. The total mass of pharmaceutical composition (e.g. comprising the BTN, SLF and ILQ and one or more excipients) contained within each capsule was about 110 mg to about 120 mg. For the 5 mg capsules and 20 mg capsules, an appropriate amount of the mixture prepared for the 50 mg capsules was filled into the capsule shells and additional MCC was added to ensure each capsule shell was full. As used in this Example, the "5 mg capsules" contained about 5.85 mg extract, the "20 mg capsules" contained about 23.4 mg extract and the "50 mg capsules" contained about 58-59 mg extract.

The relative amount of B, S and I in each capsule was measured according to the following protocol, and the results of this analysis are provided in Table 5, below. Each capsule's contents was weighed, and extracted in 50:50 EtOH:$H_2O$ (1 ml), with sonication. The samples were filtered (0.45 µm nylon) and diluted in 50:50 EtOH:$H_2O$ 1 in 10 prior to HPLC analysis to keep them within HPLC detection limits. Total capsule results have been corrected for measured mass and dilutions. Analytical reversed phase HPLC was carried out using an Agilent HP1100, controlled with Agilent OpenLab, at 20° C. on a C18 column (Phenomenex Luna ODS(3) 5 µm 100 Å 150×3 mm) with a 2×4 mm C18 guard column. The mobile phase flow rate was 0.5 ml/min, comprising MeCN (A) in $H_2O$ (B), both with 0.1% formic acid, programmed: A 10% at 0 min (t0), linearly increased to A 100% at 12.5 minutes (t12.5), held at 100% to 15 minutes (t15), linearly decreased to A 10% at 16 minutes (t16), held at 10% to 20 minutes (t20). Peaks were detected at 382 nm and quantified using response factors from calibration with pure compounds.

TABLE 5

Amounts of sulfuretin (S), butein (B) and isoliquiritigenin (I) in the capsules (excluding capsule shell) used in Example 5

| Entry | Total mass in capsule (mg) | Capsule type | S (mg) | B (mg) | I (mg) |
|---|---|---|---|---|---|
| 1 | 111.1 | 5 mg dose Rep 1 | 0.15 | 0.27 | 0.16 |
| 2 | 113.2 | 5 mg dose Rep 2 | 0.14 | 0.25 | 0.15 |
| 3 | 115.2 | 5 mg dose Rep 3 | 0.12 | 0.22 | 0.13 |
| 4 | 116.9 | 20 mg dose Rep 1 | 0.53 | 0.96 | 0.59 |
| 5 | 118.2 | 20 mg dose Rep 2 | 0.53 | 1.00 | 0.60 |
| 6 | 119 | 20 mg dose Rep 3 | 0.49 | 0.91 | 0.55 |
| 7 | 116.2 | 50 mg dose Rep 1 | 1.20 | 2.21 | 1.35 |
| 8 | 113 | 50 mg dose Rep 3 | 1.12 | 2.07 | 1.26 |
| 9 | 116.1 | 50 mg dose Rep 3 | 1.14 | 2.07 | 1.27 |

For the 5 mg unit dose (entries 1-3 of Table 5), the concentration of SLF was about 0.09 wt % to about 0.15 wt %, the concentration of BTN was from about 0.18 wt % to about 0.25 wt % and the concentration of ILQ was about 0.1 wt % to about 0.15 wt %. For the 20 mg unit dose (entries 4-6 of Table 5), the concentration of SLF was about 0.4 wt % to about 0.5 wt %, the concentration of BTN was from about 0.75 wt % to about 0.85 wt % and the concentration of ILQ was about 0.45 wt % to about 0.55 wt %. For the 50 mg unit dose (entries 7-9 of Table 5), the concentration of SLF was about 0.95 wt % to about 1.05 wt %, the concentration of BTN was from about 1.7 wt % to about 2 wt % and the concentration of ILQ was about 1 wt % to about 1.2 wt %. For each of these 3 unit doses, the ratio of SLF:BTN:ILQ was about 1:about 1.8:about 1.1.

Study Protocol: Enrollment and exposure to the compositions occurred in a sequential, expanding order. The first person recruited completed all doses, prior to dosing the next two participants. These two completed the study prior to the next four participants, and so on.

Prior to enrolment in the study, participants had an electrocardiogram (ECG) and screening blood tests, if these were not performed within the preceding 3 months, for (a) HbA1c, (b) liver function, (c) renal function, and (d) any additional tests deemed to be appropriate by the physician at the time of screening.

Participants underwent a standard 75 g oral glucose tolerance test (OGTT) after a 12 hour overnight fast. In the standard OGTT, 75 g of glucose solution is orally administered over 5 mins in the form of 222 ml of Glucola. Each participant had a venous blood sample taken at −5 minutes and 0 minutes and then 30-minute intervals for 3 hours for analysis of glucose, insulin and C-peptide concentrations. Each time point measured relative to glucose administration. Blood samples were taken in an oxalate/fluoride tube and an EDTA tube at each time point. The EDTA tubes were collected on ice. All the tubes were centrifuged within 30 minutes of collection and then transferred to a cryovial via a pipet and frozen at −80 degrees within 1 hour of collection until analysis. Plasma glucose, c-peptide and insulin concentration were determined from each sample. The results of the initial OGTT serve as "baseline" or control for glucose regulation by the participant.

Participants also attended the study centre on three further occasions at least one week apart and receive an escalating dose of the following dosage levels: (1) 15 $mg/m^2$, (2) 30 $mg/m^2$ and (3) 60 $mg/m^2$. On each of these subsequent visits, each participant received treatment with the composition of the invention one hour prior to a repeated 75 g OGTT. To achieve administration of the desired dosage, the required number of capsules as described above were administered orally with water. Blood collection and sampling was carried out identically as for the baseline OGTT test protocol described above with an additional blood sample collected prior to administration of the composition.

A full set of observations including Heart Rate, Blood Pressure, Respiratory Rate, Oxygen Saturation and Temperature was also recorded every 30 minutes for a total of five hours after the ingestion of the composition.

Results

The results for the 10 participants that have completed all four treatment sessions are outlined in Table 6 (glucose concentration), Table 7 (insulin concentration) and Table 8 (C-peptide concentration). At the time of filing this application other participants had been enrolled in the study that were yet to complete treatment at each dosage level (results not shown) and enrollment of further participants is continuing.

TABLE 6

Plasma glucose concentration (mmol/L) for all completed trial participants

| Patient ID | Event Name[A] | Time (minutes relative to glucose administration) | | | | | | | |
|---|---|---|---|---|---|---|---|---|---|
| | | −65 | −5 | 0 | 30 | 60 | 90 | 120 | 150 | 180 |
| GZA001 | 1 | — | 6.4 | 6.6 | 9.8 | 14.9 | 14.4 | 13.2 | 10.9 | 9.2 |
| GZA001 | 2 | 6.5 | 6.7 | 6.4 | 10.1 | 12.7 | 12.6 | 12.3 | 9.1 | 7.7 |
| GZA001 | 3 | 7 | 6.9 | 6.7 | 9.5 | 12.7 | 13.4 | 11.8 | 10 | 8.6 |
| GZA001 | 4 | 6.4 | 6.8 | 6.4 | 9.7 | 13.1 | 13.6 | 11.7 | 7.5 | 5.6 |
| MDU002 | 1 | — | 6.3 | 6.3 | 7.5 | 10.9 | 12.3 | 13.7 | 9.8 | 7.8 |
| MDU002 | 2 | 6.6 | 6.6 | 6.3 | 8.5 | 11.8 | 13.5 | 12.4 | 9.8 | 8.7 |
| MDU002 | 3 | 6 | 6.1 | 5.9 | 8.3 | 11.3 | 12.6 | 11.4 | 8.4 | 7.2 |
| MDU002 | 4 | 6 | 6.1 | 5.7 | 8 | 11.1 | 12.3 | 10.3 | 6.3 | 4.6 |
| KLY003 | 1 | — | 7.4 | 7.4 | 9.8 | 13.1 | 14 | 14.1 | 13.5 | 11.6 |
| KLY003 | 2 | 7.4 | 7.5 | 6.9 | 8.7 | 12 | 13.3 | 13.2 | 12.3 | 10.2 |
| KLY003 | 3 | 7.2 | 7.3 | 7 | 8.9 | 11.8 | 13.1 | 12.8 | 11.3 | 9.2 |
| KLY003 | 4 | 7.1 | 7.2 | 7 | 8.6 | 11.9 | 13.8 | 13.4 | 11.8 | 10.2 |
| SOP004 | 1 | — | 5.9 | 5.8 | 10.2 | 10.8 | 12.2 | 8.3 | 5.7 | 3.8 |
| SOP004 | 2 | 6 | 6 | 5.8 | 10.1 | 12.7 | 10.8 | 9.2 | 7.2 | 5.1 |
| SOP004 | 3 | 5.8 | 6 | 5.8 | 8.7 | 10.9 | 12.1 | 9.8 | 8.6 | 4.9 |
| SOP004 | 4 | 5.6 | 5.5 | 5.4 | 7.5 | 9.2 | 8.5 | 5.1 | 4.2 | 3.9 |
| ZPH005 | 1 | — | 8.2 | 8 | 12.1 | 15.3 | 17 | 15.3 | 12.9 | 10.4 |
| ZPH005 | 2 | 8 | 8 | 8 | 11.6 | 15.3 | 14.1 | 14.5 | 12.4 | 10.3 |
| ZPH005 | 3 | 7.8 | 7.8 | 7.7 | 15.2 | 14.9 | 14.8 | 12 | 8.7 | 6.4 |
| ZPH005 | 4 | 8.2 | 8.1 | 8.1 | 11.4 | 15.8 | 15.8 | 14 | 10.5 | 7.9 |
| UWA007 | 1 | — | — | 6.3 | 8.9 | 9.2 | 6.2 | 7.6 | 6.6 | 5.1 |
| UWA007 | 2 | 6.5 | 6.6 | 6.7 | 10.2 | 10.6 | 9.8 | 8.9 | 7.9 | 7.4 |
| UWA007 | 3 | 6.8 | 6.8 | 6.8 | 7.2 | 8.9 | 7.6 | 9.6 | 7.1 | 5.5 |
| UWA007 | 4 | 6.6 | 6.7 | 6.5 | 8.5 | 6.9 | 5.7 | 6.3 | 5.5 | 4.8 |
| LNV009 | 1 | — | 7.7 | 8.1 | 12.2 | 16.4 | 17.2 | 14.3 | 12.8 | 12.3 |
| LNV009 | 2 | 6.9 | 6.9 | 7 | 11.9 | 13.8 | 15.7 | 15 | 15.2 | 13.5 |
| LNV009 | 3 | 7.1 | 7.2 | 7.1 | 11 | 14.4 | 14.9 | 11.7 | 8.9 | 10.6 |
| LNV009 | 4 | 7.8 | 7.9 | 7.9 | 11.7 | 14.6 | 15.5 | 13.4 | 12 | 10.8 |
| JFR008 | 1 | — | 10.6 | 11.1 | 13.3 | 15.6 | 17.7 | 17.1 | 14.3 | 12.6 |
| JFR008 | 2 | 8.4 | 8.6 | 8.8 | 8.5 | 7.9 | 9.6 | 13.2 | 15.2 | 15.9 |
| JFR008 | 3 | 9.6 | 9.4 | 9.4 | 13.6 | 17 | 17.8 | 15.9 | 13.8 | 11.1 |
| JFR008 | 4 | 10.5 | 10.4 | 10.3 | 15.8 | 18.4 | 17.9 | 16.5 | 13.7 | 11.4 |

TABLE 6-continued

Plasma glucose concentration (mmol/L) for all completed trial participants

| Patient ID | Event Name[A] | Time (minutes relative to glucose administration) | | | | | | | | |
|---|---|---|---|---|---|---|---|---|---|---|
| | | −65 | −5 | 0 | 30 | 60 | 90 | 120 | 150 | 180 |
| BDA012 | 1 | — | 6.9 | 7 | 9.7 | 13.3 | 15.2 | 15.2 | 13.9 | 10.2 |
| BDA012 | 2 | 6.6 | 6.9 | 6.2 | 8.8 | 14.6 | 13.9 | 14.6 | 11 | 7.1 |
| BDA012 | 3 | 6.8 | 6.9 | 6.6 | 9.8 | 14.8 | 15.3 | 15.5 | 13 | 9.5 |
| BDA012 | 4 | 6.8 | 6.7 | 6.3 | 9.1 | 12.3 | 14.9 | 13.7 | 14.4 | 13 |
| LDX014 | 1 | — | 9 | 9.1 | 13.8 | 17.3 | 17.9 | 16.7 | 16.3 | 13.1 |
| LDX014 | 2 | 8 | 8 | 7.9 | 10.8 | 14.2 | 16.4 | 15.6 | 15 | 11 |
| LDX014 | 3 | 7.4 | 7.7 | 7.6 | 12.3 | 13.6 | 15.8 | 14.2 | 9.7 | 7 |
| LDX014 | 4 | 7.7 | 7.8 | 7.2 | 13.2 | 15.8 | 17.8 | 15 | 9.9 | 7.9 |

Notes for Table 6:

[A]Event 1 indicates baseline OGTT test only; Event 2 indicates 15 mg/m$^2$ dosage administered at time −60 minutes; Event 3 indicates 30 mg/m$^2$ dosage administered at time −60 minutes; and Event 4 indicates 60 mg/m$^2$ dosage administered at time −60 minutes.

TABLE 7

Plasma insulin concentration (pmol/L) for all completed trial participants

| Patient ID | Event Name[A] | Time (minutes relative to glucose administration) | | | | | | | | |
|---|---|---|---|---|---|---|---|---|---|---|
| | | −65 | −5 | 0 | 30 | 60 | 90 | 120 | 150 | 180 |
| GZA001 | 1 | — | 139 | 143 | 284 | 587 | 796 | 765 | 562 | 418 |
| GZA001 | 2 | 205 | 166 | 132 | 368 | 431 | 758 | 776 | 605 | 446 |
| GZA001 | 3 | 130 | 139 | 118 | N/A | 531 | 649 | 465 | 403 | 384 |
| GZA001 | 4 | 194 | 186 | 120 | 326 | H | H | 730 | 372 | 245 |
| MDU002 | 1 | — | 135 | 164 | 274 | 646 | 1002 | 1880 | 1905 | 1008 |
| MDU002 | 2 | 223 | H | 221 | 423 | 895 | 1811 | 2353 | 1746 | 1719 |
| MDU002 | 3 | 135 | 135 | 154 | 328 | 654 | 6961 | 1976 | 1584 | 984 |
| MDU002 | 4 | 122 | 121 | 149 | 286 | 731 | 1903 | 3087 | 1754 | H |
| KLY003 | 1 | — | H | H | 273 | H | 516 | H | 390 | 356 |
| KLY003 | 2 | 219 | 227 | 197 | 246 | 534 | 552 | 505 | 430 | 387 |
| KLY003 | 3 | 160 | 155 | 150 | H | 510 | H | 514 | 433 | Error |
| KLY003 | 4 | 162 | 172 | 153 | 277 | 477 | 568 | 492 | 576 | 392 |
| SOP004 | 1 | — | 284 | 293 | 1526 | 1524 | 2179 | 1452 | 637 | 235 |
| SOP004 | 2 | 298 | 307 | 204 | 1589 | H | 1617 | H | H | 437 |
| SOP004 | 3 | 153 | H | 161 | 1445 | 1438 | 1444 | 1133 | 1142 | 428 |
| SOP004 | 4 | H | 156 | 119 | 847 | 1096 | 670 | 231 | 106 | 101 |
| ZPH005 | 1 | — | 308 | 291 | 625 | 1210 | 2001 | 1605 | H | H |
| ZPH005 | 2 | 198 | 201 | 215 | H | 1116 | 1105 | 1327 | 1183 | 1314 |
| ZPH005 | 3 | 211 | 228 | 276 | 1225 | H | H | 1520 | 888 | 453 |
| ZPH005 | 4 | H | H | 267 | 627 | 1563 | H | H | 973 | H |
| UWA007 | 1 | — | H | 23 | H | H | 177 | 236 | 123 | 45 |
| UWA007 | 2 | H | H | 23 | 172 | 234 | H | H | 123 | 69 |
| UWA007 | 3 | 59 | 59 | 43 | 379 | H | 300 | 224 | 207 | 51 |
| UWA007 | 4 | 49 | H | H | 288 | 236 | 171 | 159 | 126 | H |
| LNV009 | 1 | — | H | H | 298 | H | 1180 | H | H | 723 |
| LNV009 | 2 | 163 | H | 161 | 270 | 401 | 612 | 673 | 880 | 762 |
| LNV009 | 3 | 123 | 112 | 130 | 242 | 633 | 1402 | 835 | 488 | 680 |
| LNV009 | 4 | 127 | H (71) | 161 | 357 | 558 | 1126 | 892 | 988 | 721 |
| JFR008 | 1 | — | 452 | 476 | 1394 | 1300 | 1483 | 1298 | 1073 | 1061 |
| JFR008 | 2 | H | H | 604 | H | 559 | 934 | 1381 | 1596 | 1571 |
| JFR008 | 3 | (274) H | 460 | 408 | 861 | 1212 | 1375 | 1400 | 1119 | 846 |
| JFR008 | 4 | 438 | 456 | 490 | 1119 | 1677 | 1465 | 1312 | 875 | 991 |
| BDA012 | 1 | — | 181 | 168 | 491 | H (644) | 1142 | 1187 | H (1399) | 181 |
| BDA012 | 2 | 163 | 162 | 144 | 432 | 678 | H (609) | 1437 | 1282 | H (581) |
| BDA012 | 3 | 175 | 167 | 166 | 611 | 255-H | 1600 | 1545 | 2316 | 1258 |
| BDA012 | 4 | 181 | 179 | 179 | 290 | 662 | 892 | 774 | 1208 | 991 H |
| LDX014 | 1 | — | 115 | 110 | 315 | 473 | 827 | 410 | 434 | 115 |
| LDX014 | 2 | 105 | 99 | 94 | 529 | 422 | 849 | 727 | 659 | 281 |

TABLE 7-continued

Plasma insulin concentration (pmol/L) for all completed trial participants

| Patient ID | Event Name[A] | Time (minutes relative to glucose administration) | | | | | | | | |
|---|---|---|---|---|---|---|---|---|---|---|
| | | −65 | −5 | 0 | 30 | 60 | 90 | 120 | 150 | 180 |
| LDX014 | 3 | 92 | 102 | 91 | 340 | 447 | 639 | 614 | 280 | 197 |
| LDX014 | 4 | 105 | 101 | 96 | 550 | 503 | 599 | 1704 | 450 | 300 |

Notes for Table 7:
[A]Event 1 indicates baseline OGTT test only; Event 2 indicates 15 mg/m$^2$ dosage administered at time −60 minutes; Event 3 indicates 30 mg/m$^2$ dosage administered at time −60 minutes; and Event 4 indicates 60 mg/m$^2$ dosage administered at time −60 minutes.
H indicates that blood sample was haemolysed.

TABLE 8

Plasma C-peptide concentration (pmol/L) from all completed trial participants

| Patient ID | Event Name[A] | Time (minutes relative to glucose administration) | | | | | | | | |
|---|---|---|---|---|---|---|---|---|---|---|
| | | −65 | −5 | 0 | 30 | 60 | 90 | 120 | 150 | 180 |
| GZA001 | 1 | — | 1020 | 1040 | 1390 | 2360 | 3040 | 2960 | 2720 | 2290 |
| GZA001 | 2 | 1140 | 1070 | 1040 | 1640 | 2220 | 2720 | 2820 | 3000 | 2390 |
| GZA001 | 3 | 1010 | 1040 | 1030 | 1780 | 2390 | 2940 | 2700 | 2470 | 2400 |
| GZA001 | 4 | 1340 | 1390 | 1170 | 1840 | 2580 | 3460 | 3370 | 2730 | 2010 |
| MDU002 | 1 | — | 1580 | 1600 | 2000 | 3380 | 4960 | 7130 | 6980 | 5930 |
| MDU002 | 2 | 1840 | 1880 | 1860 | 2340 | 3850 | 5710 | 7110 | 6280 | 6490 |
| MDU002 | 3 | 1440 | 1450 | 1440 | 1880 | 3080 | 5000 | 6430 | 6060 | 5510 |
| MDU002 | 4 | ND | 1290 | 1430 | 1860 | 3740 | 6490 | 7810 | 6560 | 4940 |
| KLY003 | 1 | — | 1060 | 1170 | 1610 | 2200 | 2610 | 2880 | 2690 | 2530 |
| KLY003 | 2 | 1570 | 1630 | 1470 | 1800 | 2520 | 2780 | 2980 | 2970 | 2810 |
| KLY003 | 3 | 1150 | 1180 | 1230 | 1600 | 2260 | 2570 | 2770 | 2680 | 2410 |
| KLY003 | 4 | 1220 | 1190 | 1190 | 1520 | 2080 | 2830 | 2850 | 2700 | 2630 |
| SOP004 | 1 | — | 1900 | 1920 | 3740 | 4850 | 5940 | 6490 | 3670 | 4940 |
| SOP004 | 2 | 1780 | 1870 | 1480 | 3950 | 5100 | 5000 | 5060 | 4330 | 3040 |
| SOP004 | 3 | 1450 | 1640 | 1560 | 4110 | 4570 | 5200 | 4780 | 4980 | 3220 |
| SOP004 | 4 | ND | 1210 | 1230 | ND | 4320 | 3950 | 2600 | 1840 | 1550 |
| ZPH005 | 1 | — | 1630 | 1620 | 2300 | 3460 | 4950 | 4440 | 4450 | 4050 |
| ZPH005 | 2 | 1320 | 1310 | 1390 | 2080 | 3300 | 3740 | 4180 | 4330 | 4030 |
| ZPH005 | 3 | 1440 | 1440 | 1520 | 3730 | 4360 | 4810 | 5020 | 3700 | 2850 |
| ZPH005 | 4 | 1340 | 1410 | 1530 | 2180 | 4090 | 5500 | 5220 | 3940 | 3120 |
| UWA007 | 1 | — | 387 | 388 | 1220 | 1860 | 1470 | 1900 | 1470 | 973 |
| UWA007 | 2 | 356 | 349 | 334 | 1020 | 1700 | 1840 | 1760 | 1500 | 1160 |
| UWA007 | 3 | 541 | 569 | 547 | 1360 | 2170 | 2060 | 1860 | 1890 | 967 |
| UWA007 | 4 | 481 | 436 | 437 | 1440 | 1920 | 1530 | 1570 | 1420 | 715 |
| LNV009 | 1 | — | 1690 | 1770 | 2270 | 3460 | 5340 | 5050 | 4970 | 1690 |
| LNV009 | 2 | 1740 | 1700 | 1590 | 2000 | 2480 | 3520 | 3440 | 4450 | 3770 |
| LNV009 | 3 | 1640 | 1590 | 1620 | 1930 | 3140 | 5410 | 5170 | 4380 | 4670 |
| LNV009 | 4 | 1460 | 1470 | 1660 | 2260 | 3010 | 4540 | 4690 | ND | 4660 |
| JFRO08 | 1 | — | 2090 | 2120 | 3750 | 3700 | 4250 | 3970 | 3510 | 2090 |
| JFRO08 | 2 | 1870 | 1970 | 2310 | 1920 | 2210 | 2770 | 3820 | 4190 | 4310 |
| JFRO08 | 3 | 1790 | 1900 | 1880 | 2750 | 3330 | 3610 | 3650 | 3330 | 2810 |
| JFRO08 | 4 | 2080 | 1970 | 1940 | 3150 | 4140 | 3970 | 3650 | 2970 | 3010 |
| BDA012 | 1 | — | 1570 | 1560 | 2230 | IS | 4290 | 4980 | 4720 | 1570 |
| BDA012 | 2 | 1620 | 1630 | 1550 | 2260 | 3470 | 4010 | 5660 | Error | 4350 |
| BDA012 | 3 | 1530 | 1550 | 1550 | 2710 | 3400 | 5590 | 5990 | 7320 | 5880 |
| BDA012 | 4 | 1700 | 1660 | Error | 2350 | 3150 | 4130 | 5820 | 4290 | 5180 |
| LDX014 | 1 | — | 1180 | 1180 | 1900 | 2690 | 3700 | 3330 | 3420 | 1180 |
| LDX014 | 2 | 1050 | Error | 1050 | 2340 | 2520 | 3830 | 3710 | 3890 | 2930 |
| LDX014 | 3 | 1100 | 1130 | 1110 | 2040 | 2540 | 3570 | 3730 | 2960 | 2400 |
| LDX014 | 4 | 1050 | 1100 | 1140 | 2360 | 2610 | 3400 | 5140 | 3260 | 2590 |

Notes for Table 8:
[A]Event 1 indicates baseline OGTT test only; Event 2 indicates 15 mg/m$^2$ dosage administered at time −60 minutes; Event 3 indicates 30 mg/m2 dosage administered at time −60 minutes; and Event 4 indicates 60 mg/m$^2$ dosage administered at time −60 minutes.
IS indicates that insufficient sample was collected from participant.
ND indicates that sample was not collected from participant.

Figure 18:
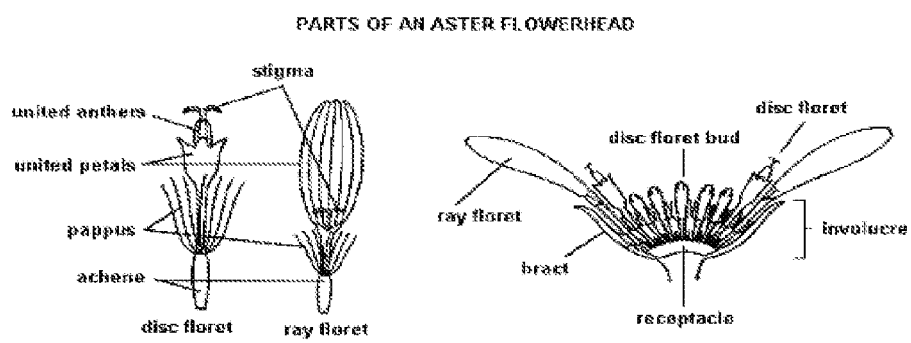
FIG. 18 shows a diagram of parts of an Aster flowerhead.
Figure 19:
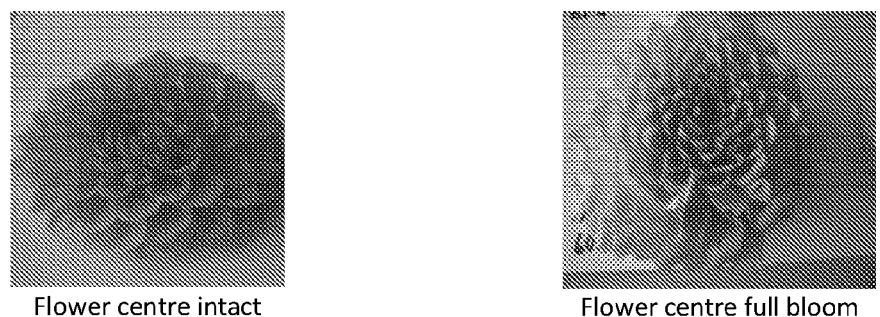
FIGS. 19A-B show photographs of *Dahlia* flower heads at different stages of development.

Data analysis: The glucose concentrations measured at 30 minute intervals from baseline to 180 minutes were summarised for the results of treatment at each dosage level (1)-(3) and the control intervention (baseline). The analyst was blinded to the details of which dosage corresponded to each dosage level (1)-(3) during the analysis. The blood glucose concentrations were combined over the 180 minutes as the 'area under the curve' (AUC) for each participant for each dosage level. The analysis includes all available data including data from participants that had completed treatment at a particular dosage level and/or baseline but had not completed treatment at all dosage levels (raw data not shown). The AUC then represents the total glucose 'exposure' over the 180 minutes. The AUCs were compared between groups using a repeated-measures ANOVA (ANalysis Of VAriance) which allows for the crossover design, each participant getting the range of dose interventions. The results from the ANOVA are summarised as means with 95% confidence intervals and dose groups compared in a pairwise manner using the least significant difference test. A two-tailed p-value<0.05 was taken to indicate statistical significance. Results of this analysis are shown in Table 9 and in FIGS. 17 and 18. Similar analysis was undertaken for the insulin and C-peptide concentration results (not shown).

TABLE 9

Calculated Area Under the Curve (AUC) based on the glucose results shown in Table 6

| Dosage | Mean | Std. Error | 95% Confidence Interval | | P-values for change in AUC compared to baseline AUC |
|---|---|---|---|---|---|
| | | | Lower Bound | Upper Bound | |
| Baseline | 2232.8 | 48.7 | 2133.8 | 2331.8 | |
| 15 mg/m$^2$ | 2105.2 | 51.3 | 2000.8 | 2209.6 | 0.080 |
| 30 mg/m$^2$ | 2157.5 | 54.4 | 2046.8 | 2268.2 | 0.310 |
| 60 mg/m$^2$ | 2041.4 | 50.1 | 1939.4 | 2143.4 | 0.010 |

Figure 22:
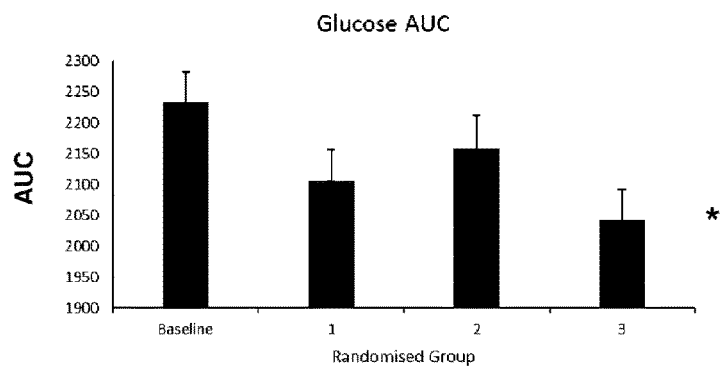
FIG. 22 shows a graph of the Area Under the Curve (AUC) determined from the glucose concentration results of Example 5 shown in FIG. 21.

All dosages demonstrated a reduction in blood glucose level. The AUC results show a statistically significant (p=0.01) reduction in glucose exposure for participants following administration of the 60 mg/m$^2$ dosage. The total reduction in glucose exposure over the OGTT corresponds to about a 9% difference in AUC when compared to the baseline (see Table 9 and FIG. 22). The results for lower dosage levels may show significance at the conclusion of the trial with the addition of further data from additional participants. Further, no side effects have been reported by participants after receiving any of the doses (15 mg/m$^2$-60 mg/m$^2$). No adverse effects have been observed in the safety blood tests; renal function, liver function or full blood count.

The invention claimed is:

1. A pharmaceutical composition in a solid unit dosage form, comprising:
    butein or a pharmaceutically acceptable salt, tautomer, solvate and/or derivative thereof (BTN); and
    sulfuretin or a pharmaceutically acceptable salt, tautomer, solvate and/or derivative thereof (SLF); and
    isoliquiritigenin or a pharmaceutically acceptable salt, tautomer, solvate and/or derivative thereof (ILQ);
    a non-aqueous, pharmaceutically acceptable excipient;
    wherein the BTN, SLF and/or ILQ are provided as an extract of a *Dahlia* plant, and the solid unit dosage form selected from a capsule, tablet, cachet, and lozenge.

2. The pharmaceutical composition of claim 1, wherein the ratio of SLF:BTN is from about 0.4:1 to about 5:1 by weight.

3. The pharmaceutical composition of claim 1, wherein the ratio of ILQ:BTN is from about 0.4:1 to about 3:1 by weight.

4. The pharmaceutical composition of claim 1, wherein the extract is of at least a petal of the *Dahlia* plant.

5. The pharmaceutical composition of claim 1, wherein the *Dahlia* plant is extracted with an extractant comprising ethanol.

6. The composition of claim 1, wherein the non-aqueous, pharmaceutically acceptable excipient is selected from one or more of dicalcium phosphate and microcrystalline cellulose (MCC).

* * * * *

UNITED STATES PATENT AND TRADEMARK OFFICE
CERTIFICATE OF CORRECTION

| | | |
|---|---|---|
| PATENT NO. | : 11,738,001 B2 | Page 1 of 1 |
| APPLICATION NO. | : 15/733131 | |
| DATED | : August 29, 2023 | |
| INVENTOR(S) | : Philip Myers Heyward et al. | |

It is certified that error appears in the above-identified patent and that said Letters Patent is hereby corrected as shown below:

On the Title Page

Item (30), delete "NZ" and insert --AU--.

Signed and Sealed this
Twenty-eighth Day of November, 2023

*Katherine Kelly Vidal*

Katherine Kelly Vidal
*Director of the United States Patent and Trademark Office*